United States Patent
Pi et al.

(10) Patent No.: US 12,219,938 B2
(45) Date of Patent: Feb. 11, 2025

(54) MOUSE MODEL OF ALCOHOL-INDUCED LIVER CANCER

(71) Applicant: UNIVERSITY OF FLORIDA RESEARCH FOUNDATION, INCORPORATED, Gainesville, FL (US)

(72) Inventors: Liya Pi, Gainesville, FL (US); Daohong Zhou, Waldo, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 85 days.

(21) Appl. No.: 17/504,752

(22) Filed: Oct. 19, 2021

(65) Prior Publication Data

US 2022/0117206 A1    Apr. 21, 2022

Related U.S. Application Data

(60) Provisional application No. 63/093,462, filed on Oct. 19, 2020.

(51) Int. Cl.
*A01K 67/027* (2024.01)

(52) U.S. Cl.
CPC ........ *A01K 67/027* (2013.01); *A01K 2207/20* (2013.01); *A01K 2207/25* (2013.01); *A01K 2227/105* (2013.01); *A01K 2267/0331* (2013.01)

(58) Field of Classification Search
None
See application file for complete search history.

(56) References Cited

U.S. PATENT DOCUMENTS 9,596,834 B2 * 3/2017 Yoneyama ........... A01K 67/027

OTHER PUBLICATIONS

Bertola A. Mouse Model of Alcoholic Steatohepatitis. Methods Mol Biol. 2020;2164:145-157. doi: 10.1007/978-1-0716-0704-6_15. PMID: 32607891. (Year: 2020).*
Laguens RP, Candela S, Hernández RE, Gagliardino JJ. Streptozotocin-induced liver damage in mice. Horm Metab Res. May 1980; 12(5):197-201. doi: 10.1055/s-2007-996241. PMID: 6446516. (Year: 1980).*
Chanda, Dipanjan et al. "Hepatic Cannabinoid Receptor Type 1 Mediates Alcohol-Inducted Regulation of Bile Acid Enzyme Genes Expression via CREBH," *PLoS One*, vol. 8, No. 7:e68845, Jul. 22, 2013, pp. 1-11, DOI: 10.1371/journal.pone.0068845.
Himabindu, B. et al. "Diabetes and Alcohol: Double Jeopardy With Regard to Oxidative Toxicity and Sexual Dysfunction in Adult Male Wistar Rats," *Reproductive Toxicology*, vol. 51, pp. 57-63, Jan. 2015, DOI: 10.1016/j.reprotox.2014.12.010.
Liu, Ken et al. "Animal Models for Hepatocellular Carcinoma Arising From Alcoholic and Metabolic Liver Diseases," *Hepatoma Research*, vol. 6, No. 7, pp. 1-16, Feb. 28, 2020, DOI: 10.20517/2394-5079.2019.39.
Fujii, Masato et al. "A Murine Model for Non-Alcoholic Steatohepatitis Showing Evidence of Association Between Diabetes and Hepatocellular Carcinoma," *Medical Molecular Morphology*, vol. 46, pp. 141-152), Feb. 22, 2013, DOI: 10.1007/s00795-013-0016-1.
Bertola, Adeline. "Rodent Models of Fatty Liver Diseases," *Liver Research*, vol. 2, No. 1, Feb. 8, 2018, pp. 3-13, DOI: 10.1016/j.livres.2018.03.001.

* cited by examiner

*Primary Examiner* — Allison M Fox
*Assistant Examiner* — Alyssa G Weston
(74) *Attorney, Agent, or Firm* — Alston & Bird LLP

(57) ABSTRACT

Described are alcohol-induced liver cancer model mice, methods of generating the alcohol-induced liver cancer model mice, and methods of using the alcohol-induced liver cancer model mice. Methods of treating alcoholic liver disease, including hepatocellular carcinoma, are also described.

14 Claims, 17 Drawing Sheets

MOUSE MODEL OF ALCOHOL-INDUCED LIVER CANCER

CROSS-REFERENCE TO RELATED APPLICATIONS

This application claims the benefit of U.S. Provisional Application No. 63/093,462, filed Oct. 19, 2020, which is incorporated herein by reference

STATEMENT REGARDING FEDERALLY SPONSORED RESEARCH OR DEVELOPMENT

This invention was made with government support under grant numbers K01 AA024174, R01 AA028035, R01 AG063801 and R01 CA219836 awarded by the National Institutes of Health. The government has certain rights in the invention.

INTRODUCTION

The liver is the largest internal organ and plays important roles in metabolism and detoxification in the body. The smallest functional unit of the liver is the hepatic acinus characterized by three metabolic zones. Each zone is centered on the line connecting two portal triads and extends outwards to the two adjacent central veins. Each portal triad contains a portal vein, hepatic artery, and bile ducts. Zone 1 refers to hepatocytes around periportal triads. The portal vein and hepatic artery bring nutrient-enriched and oxygen-enriched blood into the liver. The blood flows through sinusoids, pass hepatocytes in zones 2 and 3, and drain into central veins where they leave the liver and return to circulation systems in the body. Due to substance exchange, the blood in zone 3 has a lower oxygen concentration but high potential for toxicity from daily food intake. Therefore, there are oxygen and nutrient gradients across portal-central axis in the liver. Periportal cells in zone 1 receive the most oxygenated blood, making them less sensitive to ischemic injury but very susceptible to hepatitis viral infection. Conversely, pericentral cells in zone 3 have the poorest oxygenation and are most affected during a time of ischemia.[1] Accordingly, hepatocytes have zonation-specific functions. Zone 1 hepatocytes are important for oxidative liver functions such as gluconeogenesis, β-oxidation of fatty acids and cholesterol synthesis. Zone 3 cells are specialized for glycolysis, lipogenesis and cytochrome P-450-based drug detoxification.[2]

The liver possesses extraordinary ability to regenerate itself. It is unique among organs in its ability to fully regenerate from as little as 25 percent of its original mass. Hepatocyte proliferation is the default pathway to regenerate the liver in response to acute, minor to moderate injury. Persistent insults due to obesity, drug toxicity, alcoholism or hepatitis infection can cause chronic inflammation leading to cycles of damage and renewal, irreversible scarring, and impairment of the organ's function. Applications of lineage-tracing techniques to genetically modified reporter mouse models have revealed stemness activity of hepatocytes in all three zones. Pericentral hepatocytes in zone 3 express Wnt target genes such as axis inhibition protein 2 (Axin2), Leucine rich repeat containing G protein-coupled receptor 5 (Lgr5), and T-box transcription factor (Tbx)3. These pericentral hepatocytes have self-renewal ability in normal conditions.[3-5] Lineage tracing of Axin2, a marker of Wnt signaling pathway activation, have helped identifying a small population of hepatocytes spatially restricted to those directly adjacent to the central vein in adult mice. In health, these Axin2$^+$ cells can expand radially from the central vein to replace 40% of hepatocytes across the liver lobule. The founding Axin2$^+$ hepatocytes, which express the transcription factor Tbx, proliferate while being maintained adjacent to the central vein for at least 1 year of health.[3] The second type of hepatocytes with stemness ability are hybrid periportal cells in zone 1 expressing the biliary marker Sox9 and the hepatocyte marker HNF4a. Sox9+ HNF4a+ hybrid periportal hepatocytes can repopulate the livers during chronic liver injury such as $CCl^4$ intoxication.[6] Moreover, hepatocytes in all three zones with high telomerase activity can regenerate the livers during damage.[7] So far, little is known about how the liver regenerates, or which cells might be responsible for cancers.

Multiple risk factors including alcohol consumption, viral infections, obesity, and diabetes contribute to the genesis of hepatocellular carcinoma (HCC). Alcohol can be metabolized into the toxic intermediate acetaldehyde and alcohol-induced toxicity contributes to 3.6% of all cancers. Globally, this accounts for about 390,000 cases every year.[8] Additionally, twenty-five percent of HCC cases are associated with alcoholic liver disease (ALD).[9] As shown in FIG. 1, ALD and NAFLD have can both progress to fibrosis, cirrhosis and HCC. Non-alcoholic steatohepatitis (NASH) or alcoholic steatohepatitis (ASH) are severe forms of the two diseases that are complicated with inflammation and fibrosis. Fibrosis is reversible if the diseases are controlled. However, the diseases become irreversible when cirrhosis occurs. Cirrhotic livers are characterized by the formation of regenerative nodules that are surrounded by extensive scarring tissues. Sinusoidal vascular endothelial cells often lose fenestration leading to capillarization, and the distorted microvasculature often causes portal hypertension. These alterations induce fibrotic and hypoxic microenvironments favoring tumorigenesis. In an analysis of the Surveillance, Epidemiology, and End Results (SEER)—Medicare database for the years 1994-2007, researchers found the risk of HCC to increase 4-fold in patients with alcohol-related disorders and almost 2.5-fold in patients with diabetes and/or obesity.[12,13]

SUMMARY

Described are alcohol-induced liver cancer model mice. The model mice reproducibly induce hepatocellular carcinoma (HCC) in the setting of diabetic condition and alcoholic steatohepatitis (ASH). The model mice can be used to model ASH-associated HCC in other mammals, including human. The model mice can also be used to study alcoholic liver disease (ALD) and liver cancer. Further, the model mice can be used for drug screening and identification of biomarkers for discrete molecular and histological stages during the process of hepato-carcinogenesis in ALD.

Also described are methods of generating the alcohol-induced liver cancer model mice. The methods comprise treating the mice to induce a diabetic condition, such as by treatment with streptozotocin, and providing the mice with an alcohol-containing diet. The mice can be administered streptozotocin on about day 2 to about day 5 after birth, or about day 2 after birth. A sufficient amount of streptozotocin is administered to induce a diabetic condition. The mice can be fed the alcohol-containing diet starting in about week 7-10 after birth or about week 8 after birth. The mice can remain on the alcohol-containing diet for at least about three or at least about four months.

In some embodiments, the methods of generating an alcohol-induced liver cancer model mice are described comprising (a) administering streptozotocin to a 2-5 day old mouse in an amount sufficient to induce a diabetic phenotype in the mouse and (b) feeding the mouse an alcohol-containing diet. Streptozotocin can be administered to the mice on day 2, 3, 4, or 5 after birth. In some embodiments, the streptozotocin is administered to the mice on day 2 after birth. In some embodiments, the mice are fed an alcohol (ethanol)-containing diet starting on about day 42 to about day 70, or about day 50-63 after birth. The mice can remain on the alcohol-containing diet for at least about three or at least about four months.

In some embodiments, the alcohol-containing diet comprises an alcohol (ethanol)-liquid diet. In some embodiments, the alcohol-containing diet comprises primarily an alcohol-liquid diet. In some embodiments, the alcohol-containing diet consists of an alcohol-liquid diet. The alcohol-containing diet can contain about 30 to about 40%, about 33% to about 38%, about 35 to about 36%, about 35.5%, or about 36% of total calories from ethanol. In some embodiments, the alcohol-liquid diet contains about 5 to about 7% (v/v) ethanol. The alcohol-liquid diet can be the sole source of food.

Also described are methods of identifying biomarkers for hepato-carcinogenesis in ALD comprising generating an alcohol-induced liver cancer model mouse as described, analyzing gene expression in a tumor in the model mouse, and comparing expression of the same gene in an adjacent tissue in the same mouse or a control mouse, wherein an increase or decrease in expression of the gene relative to the adjacent tissue or control mouse indicates the gene is a biomarker for hepato-carcinogenesis in ALD.

Also described are methods of screening drugs for efficacy in preventing or treating ASH-associated HCC comprising administering the drugs to one or more of the described model mice and monitoring growth of HCC in the one or more mice.

Described are methods of treating or preventing ALD, comprising administering to a subject suffering from an ALD or a subject at risk of developing ALD a degrader for an anti-apoptotic member of the B cell lymphoma-2 (Bcl-2) family. The degrader can be a proteolysis targeting chimera (PROTAC) therapeutic. In some embodiments, the PROTAC therapeutic comprises a Bcl-xL PROTAC or a Bcl-xl and Bcl-2 dual PROTAC. In some embodiments, the Bcl-xL and Bcl-2 dual PROTAC comprises 753B. In some embodiments, the ALD comprises ethanol-induced hepato-carcinogenesis. The ALD can be, but is not limited to, ALD, ASH, or ethanol-induced hepatocellular carcinoma (EtOH-HCC).

Described are methods of treating and/or preventing EtOH-HCC in a subject identified in need thereof, the method comprising administering to the subject an effective amount of a compound 753B having the formula represented by:

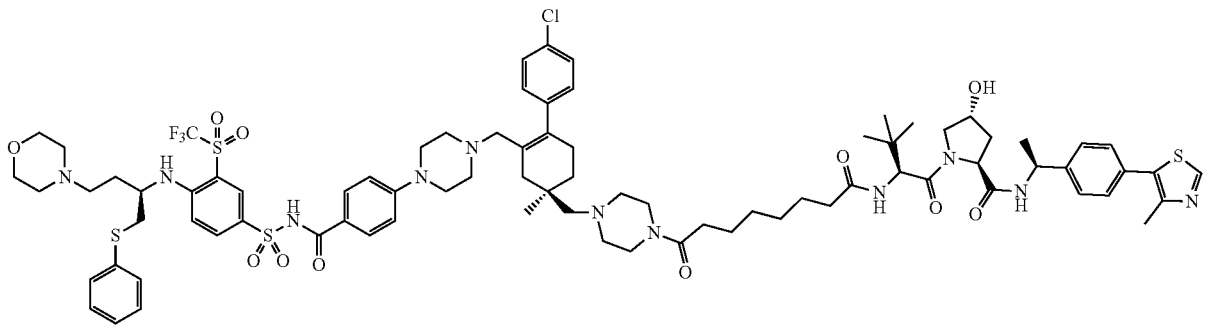 [SMILES: Cc1ncsc1-c1ccc([C@H](C)NC(=O)[C@@H]2C[C@@H](O)CN2C(=O)[C@@H](NC(=O)CCCCCCC(=O)N2CCN(C[C@]3(C)CCC(c4ccc(Cl)cc4)=C(CN4CCN(c5ccc(C(=O)NS(=O)(=O)c6ccc(N[C@H](CCN7CCOCC7)CSc7ccccc7)c(S(=O)(=O)C(F)(F)F)c6)cc5)CC4)C3)CC2)C(C)(C)C)cc1]

or a pharmaceutically acceptable salt thereof, or a pharmaceutical composition thereof. The subject may have EtOH-HCC or be at risk of developing EtOH-HCC. In some embodiments, the subject suffers from or has been diagnosed with ALD, ASH, or EtOH-HCC. Treating or preventing EtOH-HCC can comprise one or more of: decreasing expression of one or more EtOH-HCC tumor marker genes, decreasing tumor formation, decreasing tumor size, decreasing tumor number, decreasing formation of tumors, or decreasing number or size of new tumors. An EtOH tumor marker gene can be a gene that is more highly expressed in EtOH-HCC compared to expression of the gene in normal liver tissue.

Described are methods of treating and/or preventing myofibroblast cell activation associated with ALD, ASH, or EtOH-HCC in a subject identified in need thereof, the method comprising administering to the subject an effective amount of compound 753B having the formula represented by:

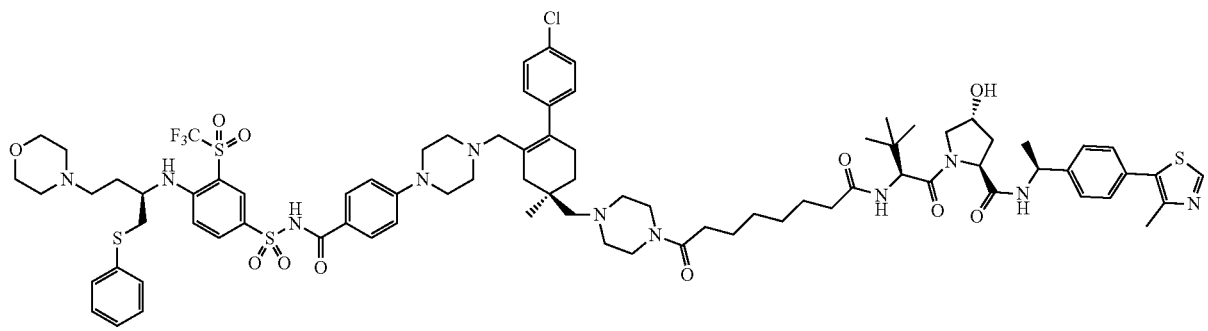 [SMILES: Cc1ncsc1-c1ccc([C@H](C)NC(=O)[C@@H]2C[C@@H](O)CN2C(=O)[C@@H](NC(=O)CCCCCCC(=O)N2CCN(C[C@]3(C)CCC(c4ccc(Cl)cc4)=C(CN4CCN(c5ccc(C(=O)NS(=O)(=O)c6ccc(N[C@H](CCN7CCOCC7)CSc7ccccc7)c(S(=O)(=O)C(F)(F)F)c6)cc5)CC4)C3)CC2)C(C)(C)C)cc1]

or a pharmaceutically acceptable salt thereof, or a pharmaceutical composition thereof. The subject may have ALD, ASH, or EtOH-HCC or be at risk of developing ALD, ASH, or EtOH-HCC.

Described are methods of treating and/or preventing liver fibrosis associated with ALD, ASH, or EtOH-HCC in a subject identified in need thereof, the method comprising administering to the subject an effective amount of compound 753B having the formula represented by:

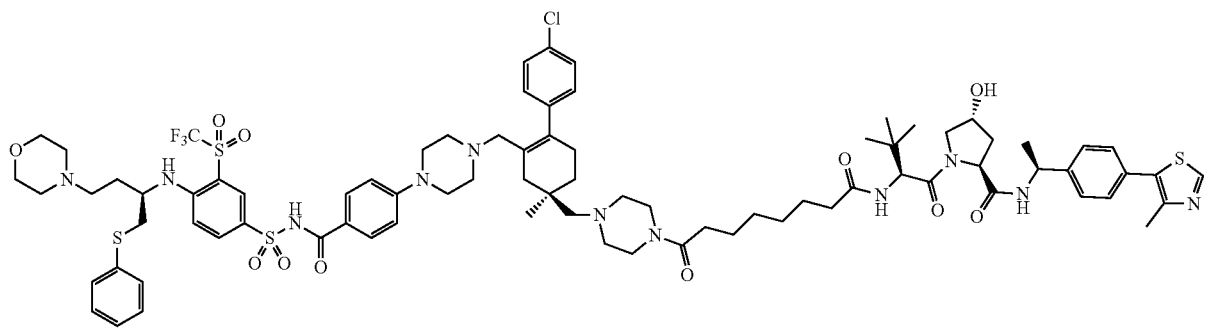 [SMILES: Cc1ncsc1-c1ccc([C@H](C)NC(=O)[C@@H]2C[C@@H](O)CN2C(=O)[C@@H](NC(=O)CCCCCCC(=O)N2CCN(C[C@]3(C)CCC(c4ccc(Cl)cc4)=C(CN4CCN(c5ccc(C(=O)NS(=O)(=O)c6ccc(N[C@H](CCN7CCOCC7)CSc7ccccc7)c(S(=O)(=O)C(F)(F)F)c6)cc5)CC4)C3)CC2)C(C)(C)C)cc1]

or a pharmaceutically acceptable salt thereof, or a pharmaceutical composition thereof. The subject may have ALD, ASH, or EtOH-HCC or be at risk of developing ALD, ASH, or EtOH-HCC. In some embodiments, the subject has or has been diagnosed with ALD, ASH, or EtOH-HCC. Treating or preventing liver fibrosis can comprise one or more of: decreasing expression of one or more fibrosis-related genes, decreasing fibrosis in the liver, or decreasing formation or development of fibrosis. A fibrosis-related gene is a gene that is more highly expressed during EtOH-associated hepatocarcinogenesis or in fibrotic liver tissue associated with ALD, ASH, or EtOH-HCC compared to expression of the gene in normal liver tissue.

DETAILED DESCRIPTION

Figure 1:
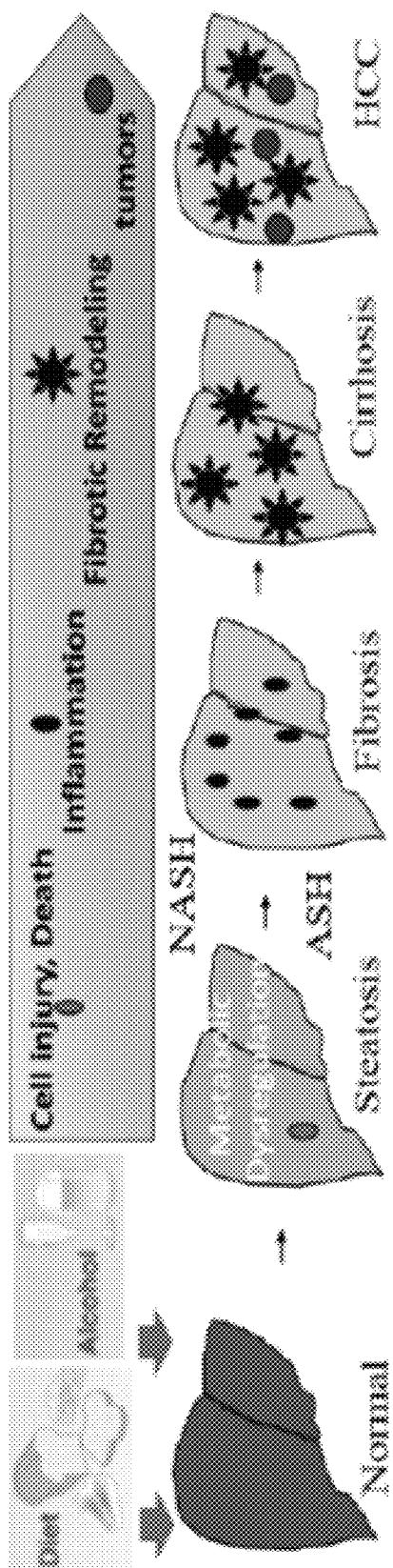
FIG. 1. Spectrums of liver pathologies in NAFLD and ALD diseases. Metabolic dysregulation causes cell injury, death, inflammation and fibrotic remodeling at steatosis, fibrosis, and cirrhosis stages. HCC may eventually develop in patients with NASH or ASH caused by high fat food or alcohol consumption.

As used herein, including the appended claims, the singular forms of words such as "a," "an," and "the," include their corresponding plural references unless the context clearly dictates otherwise. The conjunction "or" is to be interpreted in the inclusive sense, i.e., as equivalent to "and/or," unless the inclusive sense would be unreasonable in the context. Use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings.

In general, the term "about" indicates variation in a quantity of a component of a composition not having any significant effect on the activity or stability of the composition. The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0 to 20%, 0 to 10%, 0 to 5%, or up to 1% of a given value. Where particular values are described in the application and claims, unless otherwise stated the term "about" meaning within an acceptable error range for the particular value should be assumed. All ranges are to be interpreted as encompassing the endpoints in the absence of express exclusions such as "not including the endpoints"; thus, for example, "within 10-15" includes the values 10 and 15. One skilled in the art will understand that the recited ranges include the end values, as whole numbers in between the end values, and where practical, rational numbers within the range (e.g., the range 5-10 includes 5, 6, 7, 8, 9, and 10, and where practical, values such as 6.8, 9.35, etc.).

"Steatohepatitis" is a type of fatty liver disease, characterized by inflammation of the liver with concurrent fat accumulation in liver. Mere deposition of fat in the liver is termed steatosis, and together these constitute fatty liver changes.

"Fatty liver disease" (FLD) is a condition in which fat builds up to more than 5-10% of the liver's weight and may be caused alcohol abuse, fat in the blood, toxins, medication side effects, diabetes mellitus, obesity, rapid weight loss, and genetic in-heritance. FLD is divided into two common types: alcoholic fatty liver disease (AFLD) and nonalcoholic fatty liver disease (NAFLD). NAFLD was initially reported by Ludwig J et al. Mayo Clin. Proc. 1980 55, 434-438). AFLD occurs in patients who consume excessive amounts of alcohol, defined as greater than 40 to 60 g daily.

"Alcoholic Steatohepatitis" (ASH) is a chronic, progressive liver disease characterized by thickening and scarring (fibrosis) of the liver as well as possible death (necrosis) of liver tissue. ASH is brought on by excessive, prolonged alcohol use.

"Alcoholic liver disease" (ALD), also called alcohol-related liver disease or AFLD, encompasses liver manifestations of alcohol overconsumption, including fatty liver, alcoholic hepatitis, ASH, chronic hepatitis with liver fibrosis or cirrhosis. Patients with ALD are at risk for developing alcohol-induced HCC (EtOH-HCC). As such Alcoholic liver disease includes EtOH-HCC.

"Hepatocellular carcinoma" (HCC) is a common type of primary liver cancer. Hepatocellular carcinoma occurs most often in people with chronic liver diseases. Hepatocellular carcinoma is more common in people who drink large amounts of alcohol and who have an accumulation of fat in the liver.

A "tumor marker gene" is a gene whose expression is increased or decreased in a cancer cell compared to expression of the same gene in the same type of cell that is not cancerous. Tumor marker genes can be used to assess (diagnose) whether a subject has cancer or is at risk of developing cancer. Expression of tumor marker genes is also used to monitor growth of a cancer or to monitor response of a cancer to a treatment.

"Streptozotocin" (STZ) (CAS No. 18883-66-4) is an alkylating antineoplastic agent that is particularly toxic to the insulin-producing beta cells of the pancreas in mammals. It is used in medicine for treating certain cancers of the islets of Langerhans and used in medical research to produce an animal model for hyperglycemia, type 2 diabetes, or type 1 diabetes.

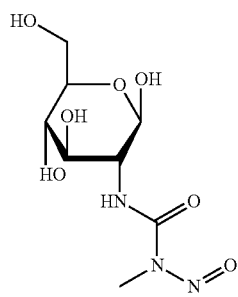

A "pharmacologically effective amount," "therapeutically effective amount," "effective amount," or "effective dose" refers to that amount of an agent to produce the intended pharmacological, therapeutic, or preventive result.

An "alcohol-liquid diet" is nutritionally balanced liquid diet containing alcohol (ethanol), provided as the sole source of food and water.

The terms "treat," "treatment," and the like, mean the methods or steps taken to provide relief from or alleviation of the number, severity, and/or frequency of one or more symptoms of a disease or condition in a subject.

B. Generation of Model Mice

Mice are initially treated to induce a diabetic phenotype. The diabatic phenotype can be induced by injecting the mice with Streptozotocin (STZ). In some embodiments, STZ is administered to mice soon after birth. In some embodiments, STZ is administered to mice on day 2, 3, 4 or 5 after birth. In some embodiments, STZ is administered to mice on day 2.

Following treatment with STZ, mice are introduced to and fed an alcohol-containing diet. In some embodiments, the alcohol containing diet is initiated at day 56±14 days week 8-10) after birth or after induction of a diabetic phenotype. In some embodiments, the mice are started on an alcohol diet starting at week eight (8) after birth.

In some embodiments, the alcohol diet contains ethanol at a level that provides 30-40% of the total energy (calories). In some embodiments, the alcohol diet contains ethanol at a level that provides 30, 31, 32, 33, 34, 35, 36, 37, 38, 39, or 40% of the total energy (calories). In some embodiments, the alcohol diet contains ethanol at a level that provides 35.5% of the total energy (calories). In some embodiments, the alcohol diet consists of an alcohol-liquid diet.

In some embodiments, the mice are introduced to the alcohol containing diet with a step-wise increase in alcohol, e.g., 0% alcohol on days 1 and 2, 1-2% alcohol on days 3 and 4, 2-3% alcohol on days 5 and 6, and 5-7% alcohol days 7 and beyond. In some embodiments, the mice are introduced to the alcohol containing diet with a step-wise increase in alcohol; e.g., increasing EtOH content by about 0.5% (v/v) each day or once in two days until the mice are consuming a diet containing 5-7% (v/v) ethanol. In some embodiments, the mice are introduced to the alcohol-liquid diet with a step-wise increase in alcohol; e.g., increasing EtOH content by about 0.5% (v/v) each day or once in two days until the mice are consuming a diet containing 5-7% (v/v) ethanol.

In some embodiments, mice on an alcohol diet receive an alcohol-liquid diet as the sole source of food.

The mice are maintained on the alcohol-containing diet for 3 or more months. In some embodiments, the mice are maintained on the alcohol-containing diet for 4 or more months. In some embodiments, the mice are maintained on the alcohol-liquid diet for 3 or more months. In some embodiments, the mice are maintained on the alcohol-liquid diet for 4 or more months.

Using the above procedure, development of ASH is observed, with progression to fibrosis, cirrhosis, and HCC. ASH-associated HCC is observed within 6 months of initiation of alcohol consumption.

Methods of Treatment

Described are methods of treating or preventing an ALD, comprising administering to a subject suffering from an ALD or a subject at risk of developing an ALD a degrader for an anti-apoptotic member of the B cell lymphoma-2 (Bcl-2) family. In some embodiments, the ALD comprises ethanol-induced hepatocarcinogenesis. The ALD can be, but is not limited to, alcoholic liver disease (ALD), alcoholic steatohepatitis (ASH), or EtOH-HCC. The degrader can be a proteolysis targeting chimera (PROTAC) therapeutic. In some embodiments, the PROTAC therapeutic comprises a Bcl-xL PROTAC or a Bcl-xL and Bcl-2 dual PROTAC. In some embodiments, the Bcl-xL and Bcl-2 dual PROTAC comprises 753B. Compound 753B has the structure represented by:

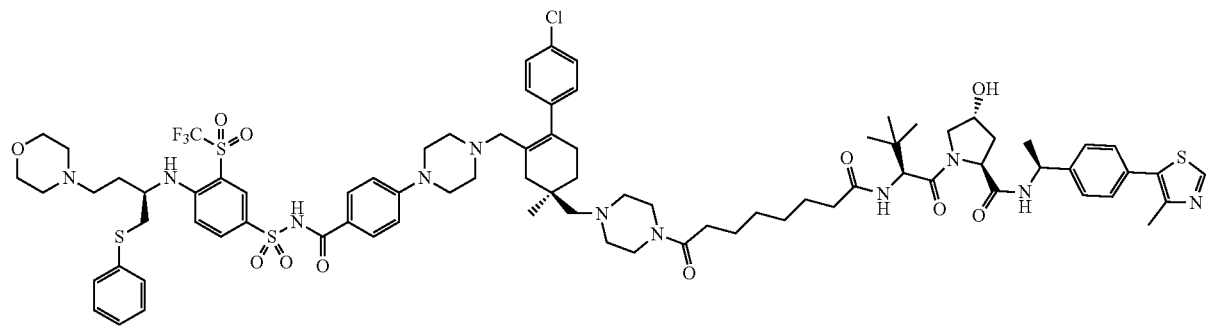 [SMILES: Cc1ncsc1-c1ccc([C@H](C)NC(=O)[C@@H]2C[C@@H](O)CN2C(=O)[C@@H](NC(=O)CCCCCCC(=O)N2CCN(C[C@]3(C)CCC(c4ccc(Cl)cc4)=C(CN4CCN(c5ccc(C(=O)NS(=O)(=O)c6ccc(N[C@H](CCN7CCOCC7)CSc7ccccc7)c(S(=O)(=O)C(F)(F)F)c6)cc5)CC4)C3)CC2)C(C)(C)C)cc1]

In some embodiments, the compound 753B is useful for treating, preventing, or managing clinical presentations associated ALD, ASH, or EtOH-HCC. In some embodiments, administration of compound 753B can be used to decrease the number, severity, and/or frequency of symptoms associated with ALD, ASH, or EtOH-HCC.

In some embodiments, the subject is a mammal, including, but not limited to, a human patient. In some embodiments, the method comprises administering a composition comprising compound 753B to a mammal to be treated.

Described are methods of treating and/or preventing EtOH-HCC in a subject identified in need thereof, the method comprising administering to the subject an effective amount of a compound 753B or a pharmaceutically acceptable salt thereof, or a pharmaceutical composition thereof. The subject may have EtOH-HCC or be at risk of developing EtOH-HCC. In some embodiments, the subject suffers from or has been diagnosed with ALD, ASH, or EtOH-HCC. Treating or preventing EtOH-HCC can comprise one or more of: decreasing expression of one or more EtOH-HCC tumor marker genes, decreasing tumor formation, decreasing tumor size, decreasing tumor number, decreasing formation of tumors, or decreasing number or size of new tumors. An EtOH tumor marker gene can be a gene that is more highly expressed in EtOH-HCC compared to expression of the gene in normal liver tissue. Compound 753B can be administered to a subject to increase survival, decrease expression of one or more EtOH-HCC tumor marker genes, decrease tumor formation, decrease tumor size, decrease tumor number, decrease formation of tumors, or decrease number or size of new tumors in a subject suffering from, diagnosed with, or at risk of developing ALD, ASH, or EtOH-HCC.

In some embodiments, administering compound 753B to a subject having EtOH-HCC reduces expression of one or more of: Gpc3, Afp, Myc, Tgfa, Cdkn2a/p16, Cdkn2b/p15, Ccl2, Ccl1, Serpine1/PAI1, and Ccl12. Administration of compound 753B to a subject having an ALD can reduce expression of the one or more genes by at least about 10%, at least about 20%, at least about 30%, at least about 40%, at least about 50%, at least about 60%, or at least about 70%.

Described are methods of treating and/or preventing myofibroblast cell activation associated with ALD, ASH, or EtOH-HCC in a subject identified in need thereof, the method comprising administering an effective amount of a compound 753B or a pharmaceutically acceptable salt thereof, or a pharmaceutical composition thereof. The subject may have ALD, ASH, or EtOH-HCC or be at risk of developing ALD, ASH, or EtOH-HCC.

Described are methods of treating and/or preventing liver fibrosis associated with ALD, ASH, or EtOH-HCC in a subject identified in need thereof, the method comprising administering an effective amount of a compound 753B or a pharmaceutically acceptable salt thereof, or a pharmaceutical composition thereof. The subject may have ALD, ASH, or EtOH-HCC or be at risk of developing ALD, ASH, or EtOH-HCC. In some embodiments, the subject has or has been diagnosed with ALD, ASH, or EtOH-HCC. Treating or preventing liver fibrosis can comprise one or more of: decreasing expression of one or more fibrosis-related genes, decrease fibrosis in the liver, or decreasing formation or development of fibrosis. A fibrosis-related gene is a gene that is more highly expressed during EtOH-associated hepatocarcinogenesis or in fibrotic liver tissue associated with ALD, ASH, or EtOH-HCC compared to expression of the gene in normal liver tissue.

In some embodiments, administering compound 753B to a subject having an ALD reduces expression of one or more of Tgf-β1, Tgf-β2, Pdgf-B, Col1a1, Col2a2, Col4a1, Col4a2, Ctgf, αSMA, and Spp1. Administration of compound 753B to a subject having an ALD can reduce expression of the one or more genes by at least about 10%, at least about 20%, at least about 30%, at least about 40%, at least about 50%, at least about 60%, or at least about 70%.

The compounds or compositions provided herein may be administered in an effective amount via a dose. Dosage may be adjusted appropriately to achieve a desired local level of the compound. The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound provided herein.

In some embodiments, the effective amount of the compound is about between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive. In certain embodiments, the effective amount includes independently between 1 mg and 3 mg, inclusive, of a compound described herein. In certain embodiments, the effective amount described herein includes independently between 3 mg and 10 mg, inclusive, of a compound described herein. In certain embodiments, the effective amount described herein includes independently between 10 mg and 30 mg, inclusive, of a compound described herein. In certain embodiments, the effective amount includes independently between 30 mg and 100 mg, inclusive, of a compound described herein.

In some embodiments, the effective amount is about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 1 mg/kg to about 25 mg/kg, about 1 mg/kg to about 20 mg/kg, about 1 mg/kg to about 15 mg/kg, about 1 mg/kg to about 10 mg/kg, or about 1 mg/kg to about 5 mg/kg of the compound. In certain embodiments, the effective amount is about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, or about 25 mg/kg of the compound.

In Vivo Administration

In pharmacology a route of administration is the path by which a drug or other substance is brought into contact with the body. In general, methods of administering drugs for treatment of a mammal are well known in the art and can be applied to administration of the described compound 753B. Compound 753B and compositions containing 753B can be administered via any suitable route in a preparation appropriately tailored to that route. In some embodiments, the pharmaceutical compositions described herein can be formulated for administration to a subject.

Pharmaceutical Composition

The compound 753B can be provided in a pharmaceutical composition or medicament. A pharmaceutical composition or medicament comprising 753B can be administered to a subject, such as a human or animal subject, for the treatment and/or prevention of symptoms and conditions associated with ALD, ASH, or EtOH-HCC.

A pharmaceutical composition or medicament includes a pharmacologically effective amount of compound 753B and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to (a) aid in processing of the drug delivery system during manufacture, (b) protect, support or enhance stability, bioavailability or patient acceptability of the API, (c) assist in product identification, and/or (d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The carrier can be, but is not limited to, a solvent or dispersion medium containing, for example, water, ethanol, polyol (for example, glycerol, propylene glycol, and liquid polyethylene glycol), and suitable mixtures thereof. A carrier may also contain adjuvants such as preservatives, wetting agents, emulsifying agents, and dispersing agents. A carrier may also contain isotonic agents, such as sugars, polyalcohols, sodium chloride, and the like into the compositions.

The pharmaceutical compositions can contain other additional components commonly found in pharmaceutical compositions. Such additional components can include, but are not limited to: anti-pruritics, astringents, local anesthetics, or anti-inflammatory agents (e.g., antihistamine, diphenhydramine, etc.). It is also envisaged that cells, tissues, or isolated organs that express or comprise the one or more of the described agents may be used as "pharmaceutical compositions".

Pharmaceutically acceptable refers to those properties and/or substances which are acceptable to the subject from a pharmacological/toxicological point of view. The phrase pharmaceutically acceptable refers to molecular entities, compositions, and properties that are physiologically tolerable and do not typically produce an allergic or other untoward or toxic reaction when administered to a subject. In some embodiments, a pharmaceutically acceptable compound is approved by a regulatory agency of the Federal or a state government or listed in the U.S. Pharmacopeia or other generally recognized pharmacopeia for use in animals and more particularly in humans.

Many modifications and other embodiments of the methods and compositions set forth herein will come to mind to one skilled in the art to which this methods and compositions pertains having the benefit of the teachings presented in the foregoing descriptions and the associated drawings. Therefore, it is to be understood that the methods and compositions are not to be limited to the specific embodiments disclosed and that modifications and other embodiments are included within the scope of the appended claims. Although specific terms are employed herein, they are used in a generic and descriptive sense only and not for purposes of limitation.

The following examples are offered by way of illustration and not by way of limitation.

EXAMPLES

Figure 2:
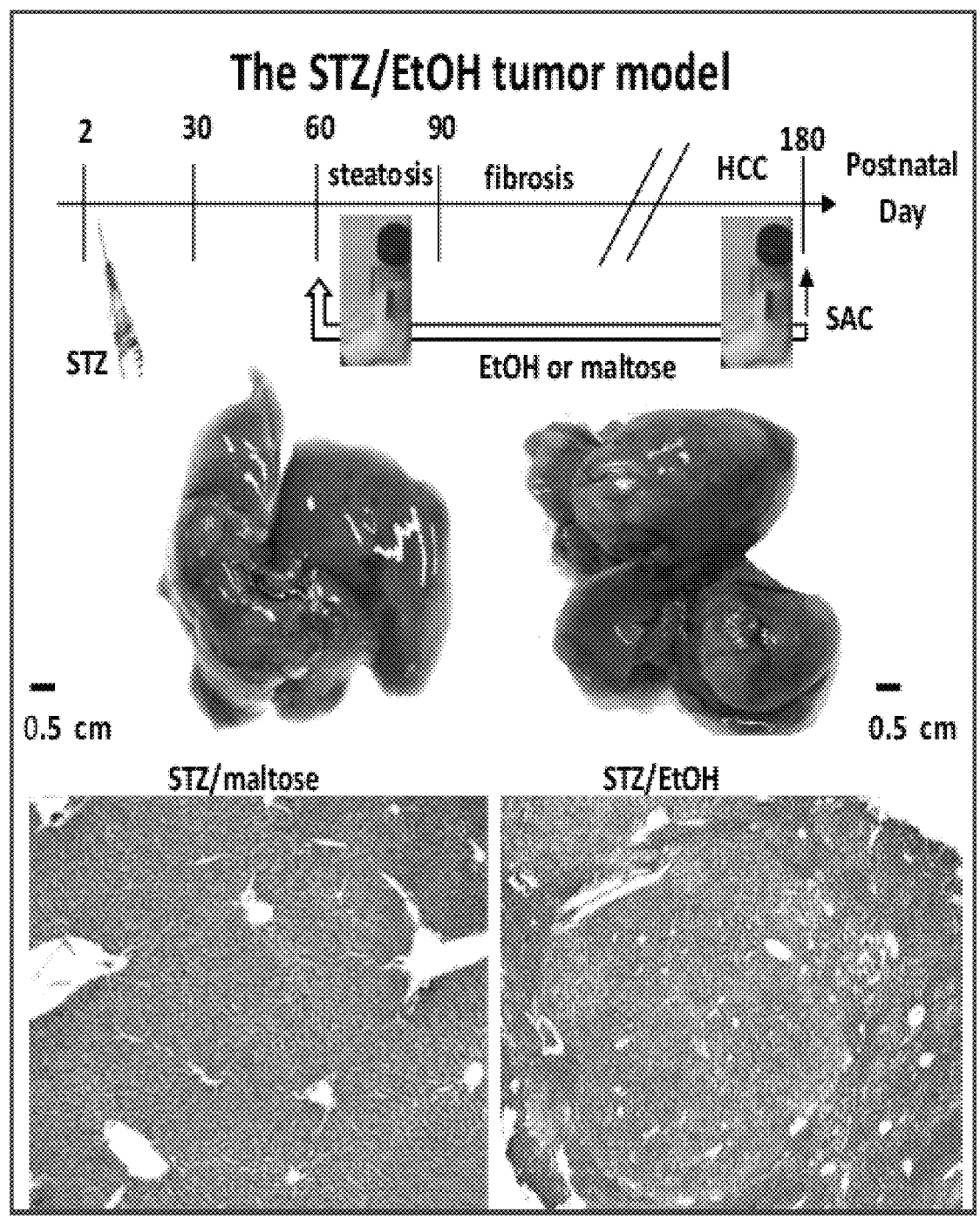
FIG. 2. HCC tumors can be induced using alcohol for ASH in STZ-treated diabetic mice. Top panel: experimental timeline. Middle panels: images of livers. Bottom panels: Images of liver sections.

Example 1. ASH-Associated HCC Appear in Diabetic Mice after Streptozotocin Administration and Four-Month-Alcohol Feeding Fujii et al. developed NASH-derived HCC model (STAM model) using STZ and HFD32.[15] This model replicates clinicopathological processes from fatty liver, NASH, fibrosis to HCC under diabetic background. The very high fat diet (HFD: 60% kcal fat) in combination with STZ also could induced morphologically detectable protrusion of liver tumor nodules at postnatal week 16. We have established a novel model in which ASH-associated liver cancer occurs in STZ-treated mice within 6 months after start of alcohol consumption (FIG. 2, 12). Mice were administered STZ on day two after birth. The STZ was administered in a dose sufficient to kill insulin-producing cells, and lead to diabetic mice. The streptozotocin-treated mice were then fed a Lieber-Decarli alcohol-liquid diet (EtOH) for four months starting at 8 weeks of age. Streptozotocin (200 μg/pup) was given through subcutaneous injection into mice at postnatal day 2. This dose was used to induce pre-diabetic condition in treated mice. This alcohol-liquid diet is from Bio-Sery (F1258) and EtOH is added into the liquid diets daily.

On day 120 post alcohol feeding, livers were analyzed for HCC genetic marker. Glypican-3 (GPC-3) and a-fetoprotein (Afp) were upregulated in both NASH and ASH tumors (Table 1). Notably, ASH-associated tumors from STZ/alcohol treated groups were larger and expressed higher levels of GPC-3 than NASH-associated tumors in STZ/HFD treated cohorts. These observations are consistent with previous literature about the greater malignancy of ASH-derived HCC compared to NASH-associated HCC in patients.

TABLE 1

Expression of HCC markers in NASH and ASH model mice.

| gene | STZ/HFD vs. adjacent tissue | | STZ/EtOH vs. adjacent tissue | |
| --- | --- | --- | --- | --- |
| | LogFC | p value | LogFC | p value |
| Glypican-3 (GPC3) | 3.7888 | 0.032 | 7.159 | 0.0016 |
| A-fetoprotein (Afp) | 4.0019 | 0.0186 | 4.2894 | 0.0149 |

Figure 3:
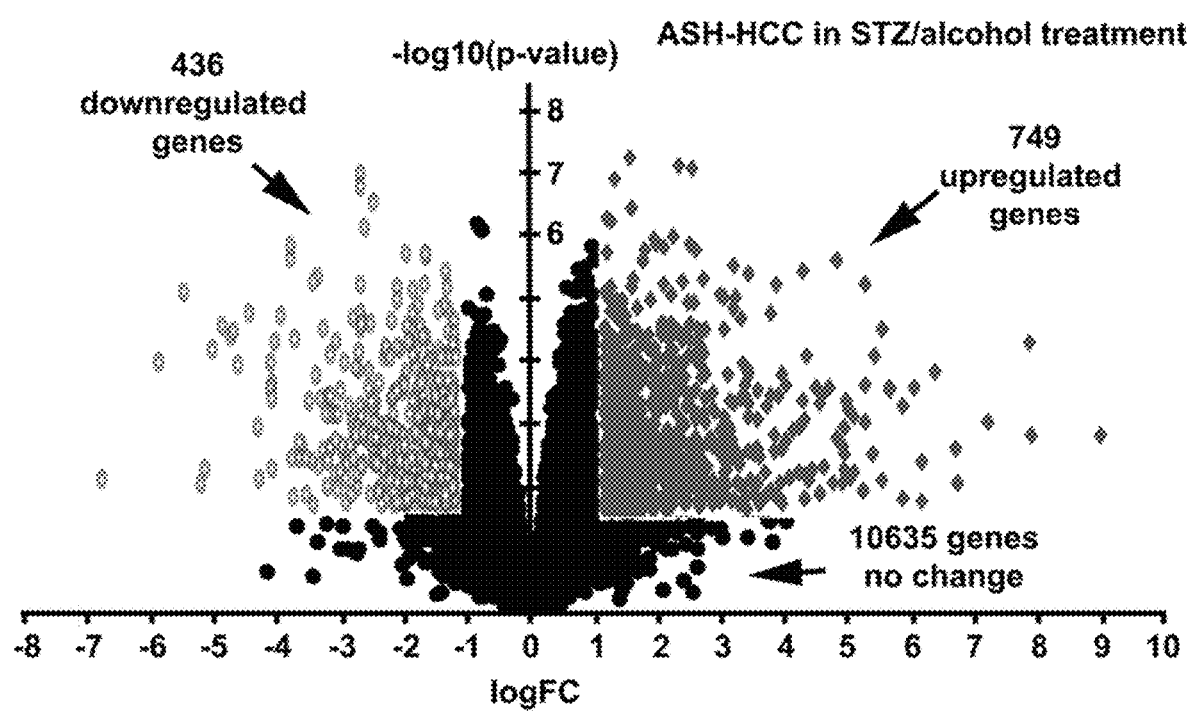
FIG. 3. Visualization of significantly up and downregulated genes identified in RNA Seq in the HCC tumors induced by the STZ/alcohol protocol.
Figure 13:
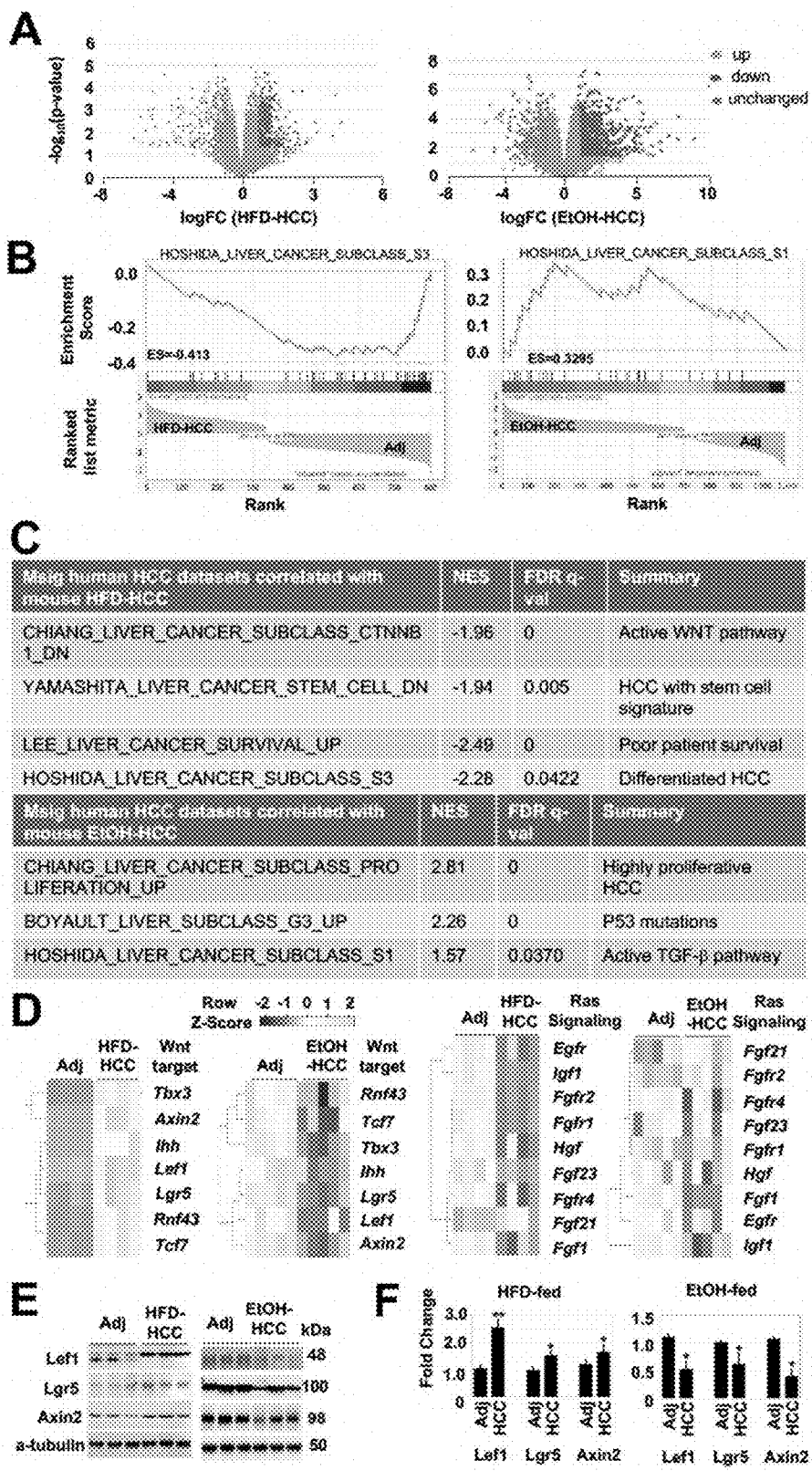
FIG. 13. RNA Sequencing shows distinct expression patterns of zonation-specific genes during HFD- and EtOH-associated hepatocarcinogenesis in the diabetic mice. (A) Scatter plots showing differentially expressed genes in the HFD- and EtOH-associated HCC compared to corresponding adjacent liver tissues after RNA seq analysis (n=4). (B) Tables summarizing significantly enriched human HCC gene sets that had correlations with mouse HFD-HCC and EtOH-HCC respectively. NES: normalized enrichment score; FDR: false discovery rate, q-val: q-values. (C) GSEA illustrating gene signature of human HCC subclass 3 that were correlated with the mouse HFD-HCC, whereas those in human HCC subclass 1 were with the mouse EtOH-HCC. (D) Heat maps showing downregulation of Ras regulators or targets in HFD-HCC. (E) A table indicated induction of multiple Wnt/b-catenin targets in HFD-HCC, but most of them were downregulated in the EtOH-HCC. (F and G) Opposite expression patterns of Wnt/β-catenin targets between HFD-HCC and EtOH-HCC were observed in Western blotting (F) and quantification by densitometry (G). Data were means±SD from three independent experiments. *P<0.05.

Example 2. RNA Sequencing Reveals Transcriptomic Changes and Upregulation of Similar Sets of Cell Cycle Regulators Between NASH and ASH-Associated HCC in Diabetic Mouse Livers To understand the molecular mechanism underlying NASH to HCC and ASH to and ASH development in the setting of a diabetic condition, we isolated RNAs of STZ/HFD or STZ/alcohol-induced tumors. Adjacent non-tumor tissues were isolated for comparison of corresponding tumors. RNA Sequencing (Seq) analysis was performed to compare whole genome transcriptomes between tumors and their control tissues. In total, 11,823 transcripts were analyzed. As shown in FIGS. 3 and 13A, 353 genes were upregulated and 534 genes were downregulated during NASH to HCC progression in the STZ/HFD treatment. In contrast, there were 749 upregulated genes and 436 downregulated genes during ASH to HCC development in the STZ/alcohol treatment.

Figure 4:
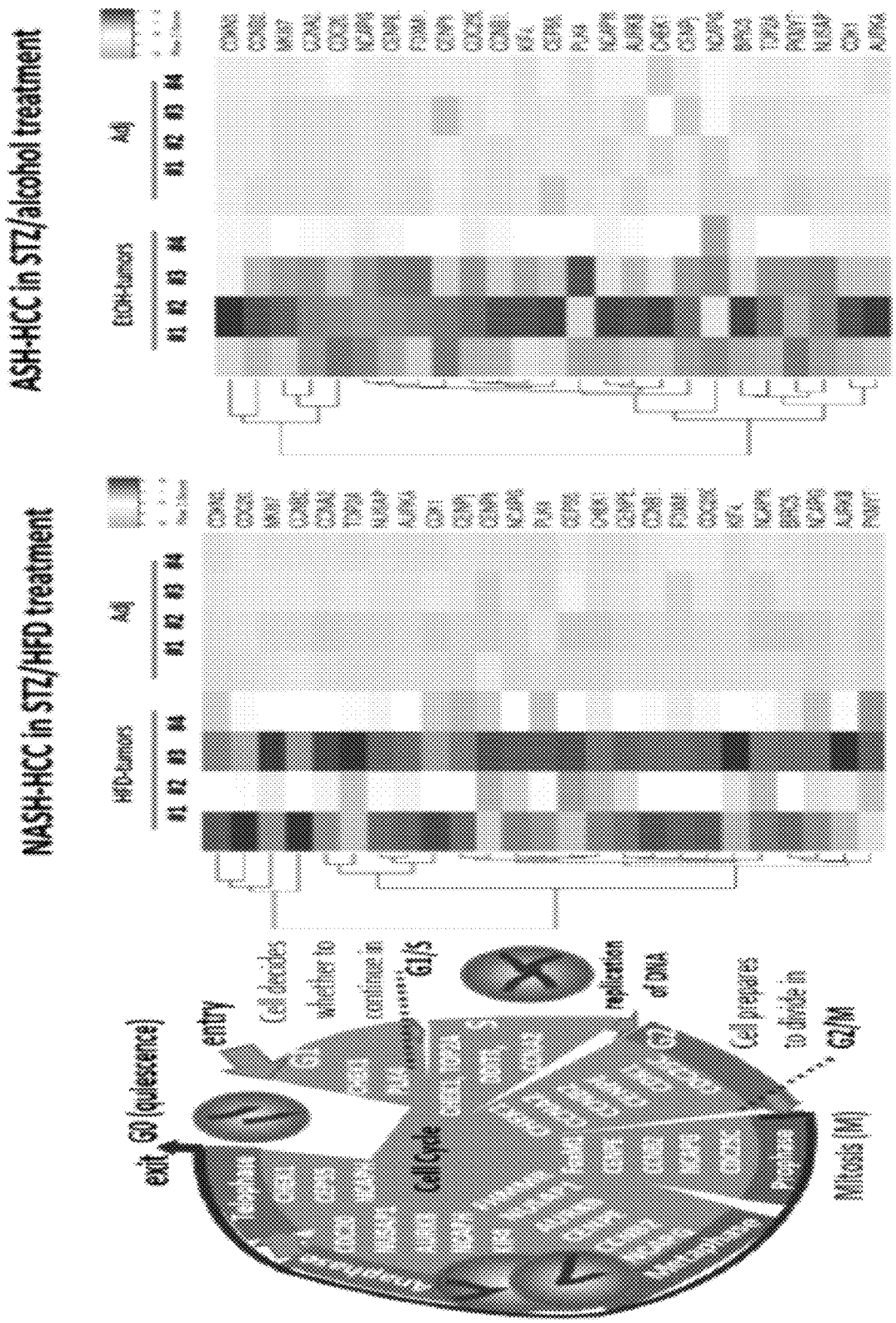
FIG. 4. Heat maps showing upregulation of similar sets of cell cycle regulators in the two types of HCC tumors induced by STZ/HFD and STZ/alcohol protocols.

About twenty-two key regulators in cell cycles were upregulated in both STZ/HFD- and STZ/alcohol-induced tumors. These regulators included Aurkb (Aurora Kinase B), CHEK1 (Checkpoint kinase 1), PLK1 (Polo-like kinase 1), PLK4 (Polo-like kinase 4), TOP2A (Topoisomerase (DNA) IIα), DDIT3 (DNA damage-inducible transcript 3), also known as C/EBP homologous protein (CHOP), CCNA2 (Cyclin-A2), CCNB1 (cyclin-B1), CCNB2 (cyclin-B2), CDC20 (cell-division cycle protein 20), CENPE (Centrosome-associated protein E), NCAPG (non-SMC condensin I complex, subunit G), NUSAP1 (Nucleolar And Spindle Associated Protein 1), NCAPH (Non-SMC Condensin I Complex Subunit H), KIF4 (chromosome-associated kinesin), CEP55 (Centrosomal protein 55), CDCl25C (M-phase inducer phosphatase 3), CDK1 (cyclin dependent kinase 1), FOXM1 (Forkhead box M1), CDKN3 (Cyclin Dependent Kinase Inhibitor 3), BIRC5 (Baculoviral IAP repeat-containing protein 5), and ETS2 (Euro Truck Simulator 2). A diagram in FIG. 4 indicates distributions of these regulators in G1, S, G2, and M (prophase, metaphase, anaphase, and telophase) phases. When leaving the G0 phase to enter into the cell cycle, cells check the integrity of chromosomes and proteins required for replication. Further, Ingenuity Canonical Pathway Analysis revealed that CCNB1, CCNB2, CDK1, CDKN1A, CHEK1, PKMYT1, PLK1, and TOP2A were involved in G2/M DNA damage checkpoint regulation [−log(p-value)=3.18 and ratio: 0.184, and Z-score=−1]. During mitosis, the localization of centrosomes and spindles is well organized to perform accurate separation of the two daughter cells. NCAPH, CENPE, KIF4, CEP55, and NUSAP1 participate in mitotic spindle regulation and mitotic processes.[36] FoxM1 and AURKB are also key regulators of mitosis.[37] Overexpression of similar gene clusters in cell cycle regulation was observed in the two types of tumors, indicating utilization of the same machinery for proliferation during ASH and NASH transition to HCC in the diabetic livers.

Example 3. GSEA Analysis Reveals that ASH-Associated HCC by STZ and HFD Belong to Hoshida Subclass S1 Characterized by Activation of TGF/3 Signaling and Upregulation of P53 Signature, while NASH-Associated HCC Caused by STZ and HFD Belong to Hoshida Subclass S3 with Well-Differentiated Characteristics Whereas Three robust HCC subclasses (termed 51, S2, and S3) have been classified in human patients according to Hoshida et al., (Cancer Research 2009). Each subclass is correlated with clinical parameters such as tumor size, extent of cellular differentiation, and serum alpha-fetoprotein levels. S1 reflected aberrant activation of the WNT signaling pathway. S2 was characterized by proliferation as well as MYC and AKT activation. S3 was associated with hepatocyte differentiation. Functional studies indicated that the WNT pathway activation signature characteristic of S1 tumors was not simply the result of β-catenin mutation but rather was the result of transforming growth factor-β activation. Thus, representing a new mechanism of WNT pathway activation in HCC.

Figure 5:
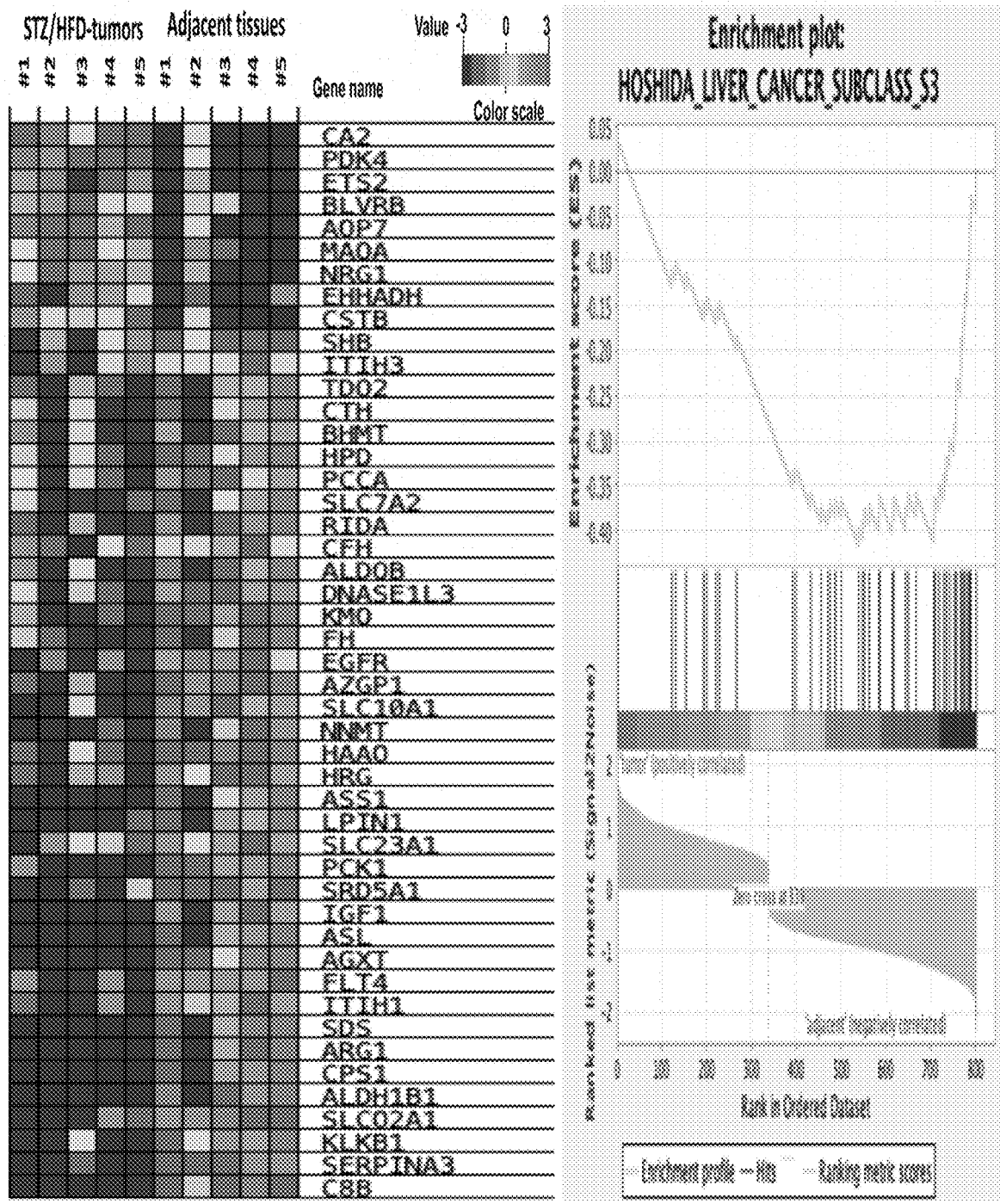
FIG. 5. The STZ/HFD tumors belong to Hoshida subclass S3 with well-differentiated characteristics in GSEA analysis.

Our Gene Set Enrichment Analysis (GSEA) revealed that the STZ/HFD-induced tumors resembled subclass 3 (S3) of human HCC characterized by hepatocyte differentiation and aberrant Wnt/β-catenin signaling (FIG. 5). These tumors also had negative correlations with human liver cancer gene sets involved in active Wnt pathway (CHIANG_LIVER_CANCER_SUBCLASS_CTNNB1_DN), HCC with stem cell signature (YAMASHITA_LIVER_CANCER_STEM_CELL_DN) and poor patient survival (LEE_LIVER_CANCER_SUBCLASS_S3) (FIG. 13C).

The dominant role of Wnt/β-catenin signaling governs metabolic zonation and regulates pericentral pathways including glutamine synthesis, drug metabolism, bile acid, and heme synthesis.[40] Upregulation of Wnt pathways regulators can be indicated by universal β-catenin targets Axin2, a ring-type E3 ubiquitin ligase (RNF)[43], lymphoid enhancer binding factor 1 (Lef1), transcription factor 7 (Tcf7), Indian hedgehog signaling molecule (Ihh), Tbx3, and Lgr5. Heatmaps illustrated upregulation of these Wnt/b-catenin downstream targets in the HFD-induced HCCs after RNA Seq analysis (FIG. 13D). Western blotting and quantification by densitometry confirmed overexpression of Wnt/b-catenin target proteins in the HFD-induced HCCs (FIGS. 13E and F). These observations were consistent previous reports about a specific transcriptomic profile with overexpression of classical target genes like GLUL and LGR5 in HCC with mutation for CTNNB1.[55]

Rat sarcoma (RAS) is a critical regulator for HCC development. Liver tumors carrying activating mutations in either the Ha-ras or the ctnnb1 gene show dominant expression patterns of periportal or pericentral hepatocytes, indicating opposing signaling pathways triggered by Ha-ras- and β-catenin-dependent factors.[56] When β-catenin signaling is induced, periportal functions have been found to be downregulated.[43] Consistent with these previous reports, we observed that HFD-HCC had low levels of periportal genes in Ras signaling but upregulation of the inhibitor histidine phosphatase (Lhpp) in HFD-induced HCC. Growth hormones such as hepatocyte growth factor (Hgf) trigger Ras signaling. Multiple growth hormones Hgf, insulin-like growth factor (Igf)1, fibroblast growth factor (fgf)23, and fibroblast growth factor (fgf)21 were decreased in HFD-HCC (FIG. 13D). Inhibited expressions of receptors including fgfr1, fgfr2, fgfr4, and epidermal growth factor receptor (Egfr) were also detected (FIG. 13D). Fgf21 is negatively regulated by Ras signaling[21], and this gene was upregulated in the HFD-induced HCC (FIG. 13D). Periportal genes included Cyp2f2 in monooxygenation, Sult5a1 in conjugation in drug metabolism, Pck1, G6Pase, and FBPase in gluconeogenesis, and Gls2 (glutaminase2) for glutamiolysis.[40] Cyp2f2 had 11.6-fold decrease (p=6.65×105), Sult5a1 had 53.4-fold reduction (p=5.72×105), Pck1 7.52-fold decrease (p=0.0002), G6Pase 2.75-fold decrease (p=0.013), and FBP1 3.42-fold decrease (p=5.75×105), Gls2 76.63-fold decrease (p=2.16E-06) in HFD-HCC.

Figure 14:
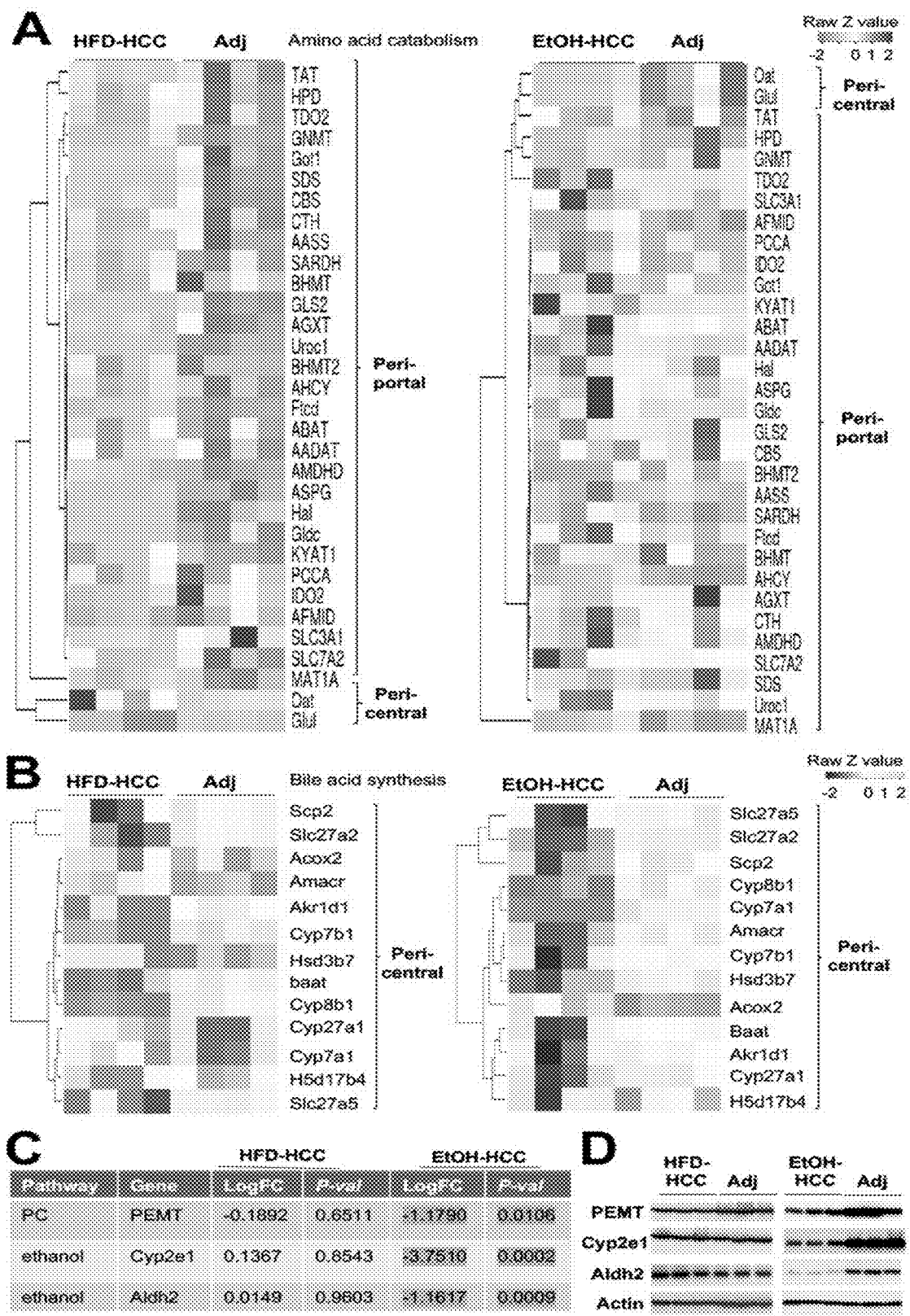
FIG. 14. Distinct expression patterns of zone-specific metabolic genes between HFD-HCC and EtOH-HCC in the diabetic mice. (A) Heatmap analyses of zone-specific profiles in amino acid catabolism indicated downregulation of periportal signature but upregulation of pericentral genes in HFD-HCC, whereas there were mosaic patterns of periportal signature and downregulation of pericentral genes in EtOH-HCC. (B) Heatmap analyses of pericentral signature indicated enhanced downregulation of genes in bile acid synthesis in EtOH-HCC compared to HFD-HCC. (C and D) Downregulation of pericentral genes including PEMT, Cyp2e1, and Aldh2 in EtOH-HCC, but not HFD-HCC in RNA Seq analysis (C) and Immunoblotting (D). PC: phosphatidylchorine.

Amino acid catabolism mainly occurs in periportal zones. Heatmaps demonstrated uniform down-regulation of more than 30 genes encoding periportal enzymes in the HFD-induced tumors (FIG. 14A). These genes (enzymes) are HAL (histidase), UROC1 (Urocanate hydratase), AMDHD1 (Amidohydrolase Domain Containing 1), and FTCD (formimidoyltransferase cyclodeaminase) in histidine degradation, IDO2 (Indoleamine 2,3-Dioxygenase 2) in tryptophan metabolism, CTH (cystathionine beta-synthase), AHCY (Adenosylhomocysteinase), CBS (cystathionine beta-synthase), MAT1a (Methionine adenosyltransferases), BHMT (Betaine-Homocysteine S-Methyltransferase), BHMT2, GNMT (Glycine N-methyltransferase) in methionine metabolism; AASS (alpha-aminoadipic semialdehyde synthase) in lysine degradation, SDS (serine dehydratase) in sulfur amino acid metabolism and threonine degradation, GLDC (Glycine decarboxylase) and SARDH (Sarcosine dehydrogenase) in glycine catabolism, GOT1 (glutamic-oxaloacetic transaminase), Cps1 (carbamoyl-phosphate synthetase 1), OTC (ornithine transcarbamylase), ASS1 (argininosuccinate synthetase), ASL (argininosuccinate lyase), and ARG1 (arginase 1) in Urea cycle, and GOT2 (glutaminase 2) in glutaminolysis. In contrast, mosaic expression patterns of these periportal genes were found in EtOH-induced tumors (FIG. 14A). In contrast, four pericentral genes that are Wnt/b-catenin targets—Glu1 coding for glutamine synthetase, Oat for ornithine aminotransferase, Rhbg (an ammonia transporter protein Rh Family B Glycoprotein), and Slc22a3 for organic cationic transporter3 were upregulated in the HFD-induced murine HCC (FIG. 14A). These results indicated that HFD-induced HCC displayed "pericentralization" phenotypes characterized by upregulation of pericentral-specific genes in Wnt/β-catenin pathways and glutamate metabolism. These tumors also had "deperiportalization" characteristics based on downregulation of periportal-specific genes in urea cycle, amino acid metabolism, and growth hormone signaling.

Figure 6:
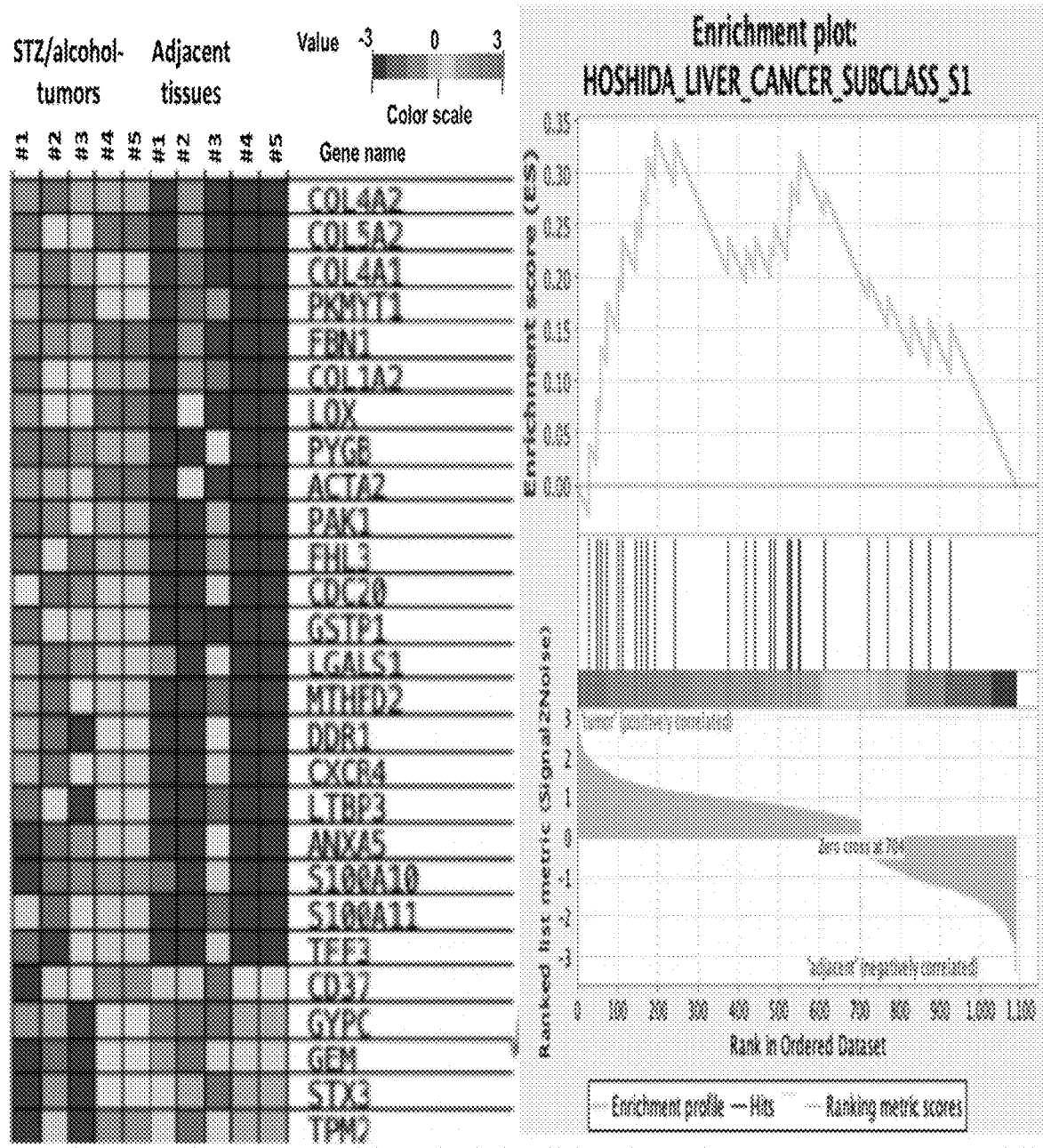
FIG. 6. The STZ/alcohol tumors belong to Hoshida subclass S1 with TGF-β and Wnt up, P53 mutation in GSEA analysis.
Figure 7:
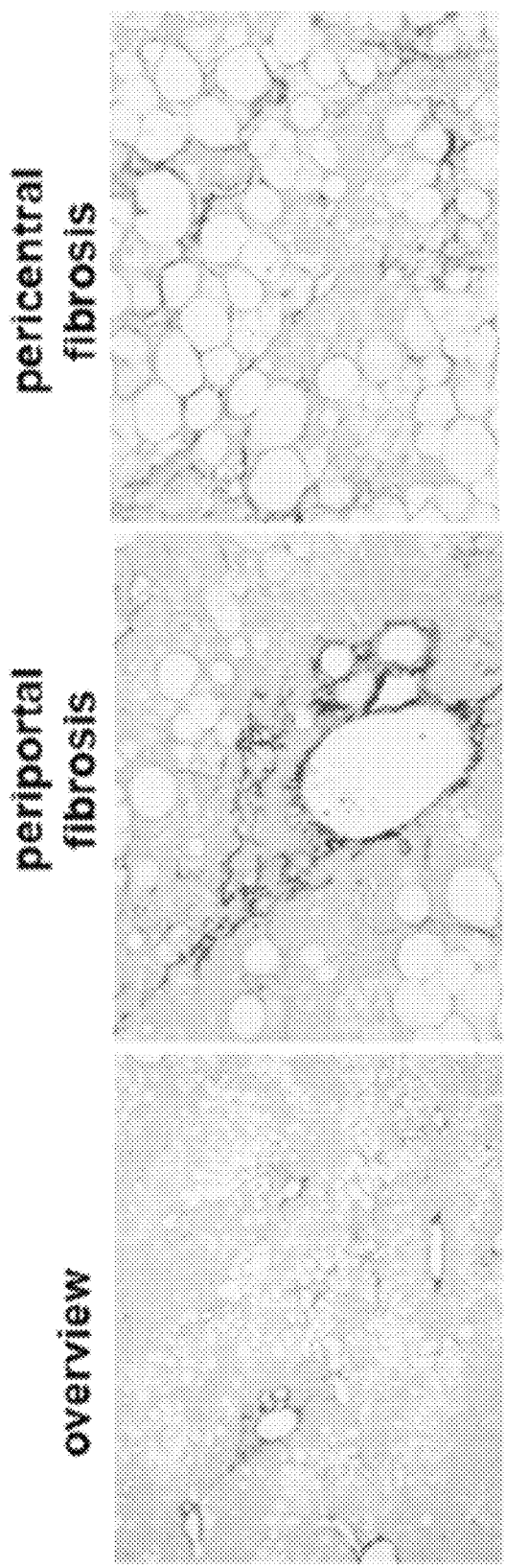
FIG. 7. Periportal and pericentral fibrosis were observed in ASH livers caused by STZ and alcohol.

In contrast, the STZ/alcohol-induced tumors were similar to Hoshida subclass 1 (S1) of human HCC. STZ/alcohol-induced tumors were characterized by pericentral downregulation of genes in Wnt/beta-catenin signaling, bile acid synthesis, phosphatidylcholine metabolism, and EtOH detoxification (FIG. 6). Both periportal and pericentral fibrosis were observed in ASH livers caused by STZ and alcohol (FIG. 7).

GSEA was also performed to compare transcriptomes of the EtOH-induced tumors with those in human HCC based on molecular signature database. The EtOH-induced tumors in diabetic murine livers displayed gene signatures similar to Hoshida subclass S1 in human HCC, which is characterized by transforming growth factor (Tgf)-β activation (FIGS. 13B and C). These tumors also had positive correlations with human liver cancer gene sets involved in highly proliferative HCC (CHIANG LIVER CANCER SUBCLASS PROLIFERATION UP) and P53 MUTATIONS (BOYAULT LIVER SUBCLASS G3 UP) (FIG. 13C). Surprisingly, EtOH-associated hepatocarcinogenesis was depericentralized. Rnf43, Tcf7, Tbx3, Ihh, Lgr5, Lef1, and Axin2 in the Wnt/β-catenin pathway were downregulated in the EtOH-induced HCC (FIG. 13D-F). Glu1 and Oat in glutamate metabolism were also underrepresented (FIG. 14A). Downregulation was also found in Lect2 (Leukocyte Cell Derived Chemotaxin 2) with 4.538-fold decrease (p=0.018), CPDX (coproporphyrinogen oxidase) with 1.392-fold reduction (p=0.0001), AhR (Aryl hydrocarbon receptor) with 1.19-fold decrease (p=0.003), and Rhbg with −5.86-fold reduction (p=0.0013), Car with −1.91 fold decrease (p=0.006).

The depericentralization phenotype in the EtOH-induced tumors was also evidenced by downregulated genes in bile acid synthesis. These genes include CYP7A1 (cholesterol 7α-hydroxylase), CYP27A1 (steroid 27-hydroxylase), 3β-HSD (3β hydroxysteroid dehydrogenase), CYP8B1 (Sterol 12-hydroxylase), S1c27a5 (Bile acyl-CoA synthetase), Scp2 (Sterol carrier protein 2), and ACOX2 (Acyl CoA Oxidase 2). EtOH-induced HCC had greater decrease based on downregulation of almost all genes except Acox2, whereas HFD-induced HCC only had decreased levels of Cyp7b1 and Cyp8b1 mRNAs in bile acid synthesis (FIG. 14B).

Phosphatidylethanolamine N-methyltransferase (PEMT) controls phosphatidylcholine metabolism, which takes place in pericentral hepatocytes.[57] Despite no change of PEMT gene in the HFD-induced HCC, this gene had 2.358-fold decrease (p val=0.0105) at the mRNA and protein levels in EtOH-induced HCC compared to their adjacent liver tissues (FIGS. 14C and D). Moreover, cytochrome p450 (Cyp)2E1 and acetaldehyde dehydrogenase (Aldh)2, two critical regulators for ethanol detoxification in pericentral hepatocytes (PMID: 32143280), were significantly reduced at mRNA and protein levels in the EtOH-induced HCC (FIGS. 14C and D). These results confirmed depericentralization feature during hepatocarcinogenesis caused by chronic ethanol exposure.

mRNA levels of fibrotic related genes were much higher in the ASH-HCC transition induced by the STZ/alcohol protocol in comparison to NASH-HCC development by the STZ/HFD treatment as shown in Table 2. Accordingly, more upregulation of P53 signatures was also found in the ASH-HCC transition (Table 3).

TABLE 2

Upregulation of profibrotic genes and regulators (bold) in ASH-HCC development induced by STZ/alcohol treatment.

| Profibrotic gene | STZ/HFD vs. adjacent tissue | | STZ/EtOH vs. adjacent tissue | |
|---|---|---|---|---|
| | LogFC | P value | LogFC | P value |
| Ctgf | −0.602 | 0.2983 | 1.3169 | 0.03227 |
| aSMA | 0.7269 | 0.1294 | 1.2806 | 0.01295 |
| col1a | 0.4102 | 0.4932 | 1.8684 | 0.00611 |
| col1b | 0.2381 | 0.6081 | 1.1596 | 0.02143 |
| col4a1 | 0.8948 | 0.0409 | 1.5876 | 0.00111 |
| col4a2 | 0.706 | 0.0632 | 1.2926 | 0.00202 |
| spp1 | −0.814 | 0.4162 | 2.5648 | 0.02191 |
| Pdgfb | 0.6801 | 0.2323 | 1.6818 | 0.00717 |
| ecm1 | −0.156 | 0.8058 | −1.756 | 0.01325 |
| Tgfb1 | −0.147 | 0.6584 | 0.0697 | 0.83292 |
| Tgfb2 | 1.1773 | 0.0278 | 1.2897 | 0.01717 |
| Tgfb3 | 0.5467 | 0.0278 | 0.9429 | 0.07913 |

TABLE 3

More upregulation of P53 signature (bold) in ASH-HCC development induced by STZ/alcohol treatment than NASH-HCC transition by STZ/HFD treatment.

| Gene | STZ/HFD vs. adjacent tissue | | STZ/EtOH vs. adjacent tissue | |
|---|---|---|---|---|
| represses by p53 | LogFC | P value | LogFC | P value |
| BIRC5 (Survival) | 1.2135 | 0.0037 | 1.4278 | 0.0011 |
| CDKN1A | 0.7728 | 0.2064 | 1.9999 | 0.00393 |
| CHEK1 | 1.2706 | 0.0013 | 1.1909 | 0.00235 |
| E2F1 | 0.4612 | 0.1503 | 1.4712 | 0.00014 |
| PIK3R3 | 0.4137 | 0.0761 | 1.2763 | $1.5 \times 10^{-5}$ |
| TNFRSF1-b | 1.1383 | 0.0306 | 3.3129 | $5.67 \times 10^{-6}$ |

Example 4. NASH-Associated HCC Caused by STZ/HFD Treatment Show Activation of Wnt/β-Catenin Pathways, Implicating Elevated Sternness Activity of Pericentral Hepatocytes, Whereas Opposite Phenotypes are Found in ASH-Associated HCC Caused by STZ/Alcohol Treatment Distinct activation of target genes in Wnt/β-catenin pathways was observed. Wnt/β-catenin activation requires interactions of Lgr5 and a ring-type E3 ubiquitin ligase (RNF)43 leading to release of β-catenin into the nucleus where it binds to transcriptional factors such as lymphoid enhancer binding factor 1 (Lef1) or transcription factor 7 (Tcf7). This leads to induction of target genes. In NASH-HCC development by STZ/HFD treatment, we found significant upregulation of multiple target genes in the Wnt/β-catenin signaling (Table 4). These genes included Lgr5, Axin2, Tbx3, RNF43, Lef1, Tcf7, and Indian hedgehog signaling molecule (Ihh) and all were specifically expressed in peri-central zones. Conversely, most of these genes were downregulated in ASH-associated HCC after STZ/alcohol treatment (Table 4). Since many of these Wnt/β-catenin target genes are stemness markers expressed in pericentral hepatocytes, we concluded that NASH-HCC developments involved activation of pericentral hepatocytes, whereas the activation of these pericentral hepatocytes seemed to be inhibited during ASH-HCC transition caused by STZ/alcohol treatment.

TABLE 4

Differential Wnt/β-catenin activation in NASH or ASH-associated HCC. Activation of pericentral related Wnt/β-catenin pathways in NASH to HCC development by STZ/HFD treatment and ASH to HCC transition after STZ/alcohol treatment. Significantly upregulated genes are in bold and significantly downregulated genes are italicized.

| Zone | Wnt/β-catenin target | STZ/HFD vs. adjacent tissue | | STZ/EtOH vs. adjacent tissue | |
|---|---|---|---|---|---|
| | | LogFC | P value | LogFC | P value |
| pericentral | Lgr5 | 1.50 | $4.0 \times 10^{-3}$ | *−2.77* | *$1.4 \times 10^{-3}$* |
| pericentral | Axin2 | 1.80 | $1.0 \times 10^{-2}$ | *−2.35* | *$2.4 \times 10^{-3}$* |
| pericentral | Tbx3 | 1.15 | $1.2 \times 10^{-2}$ | *−2.27* | *$4.10 \times 10^{-5}$* |
| pericentral | RNF43 | 1.43 | $1.3 \times 10^{-2}$ | *−1.21* | *$3.2 \times 10^{-2}$* |
| pericentral | Lef1 | 2.21 | $1.3 \times 10^{-2}$ | *−2.03* | *$3.9 \times 10^{-2}$* |
| pericentral | Tcf7 | 1.29 | $1.4 \times 10^{-2}$ | −0.97 | $6.0 \times 10^{-2}$ |
| pericentral | Ihh | 1.67 | $1.7 \times 10^{-2}$ | *−2.35* | *$3.7 \times 10^{-3}$* |
| pericentral | Glu1 | 1.28 | $2.6 \times 10^{-2}$ | *−2.78* | *$7.96 \times 10^{-5}$* |

Figure 8:
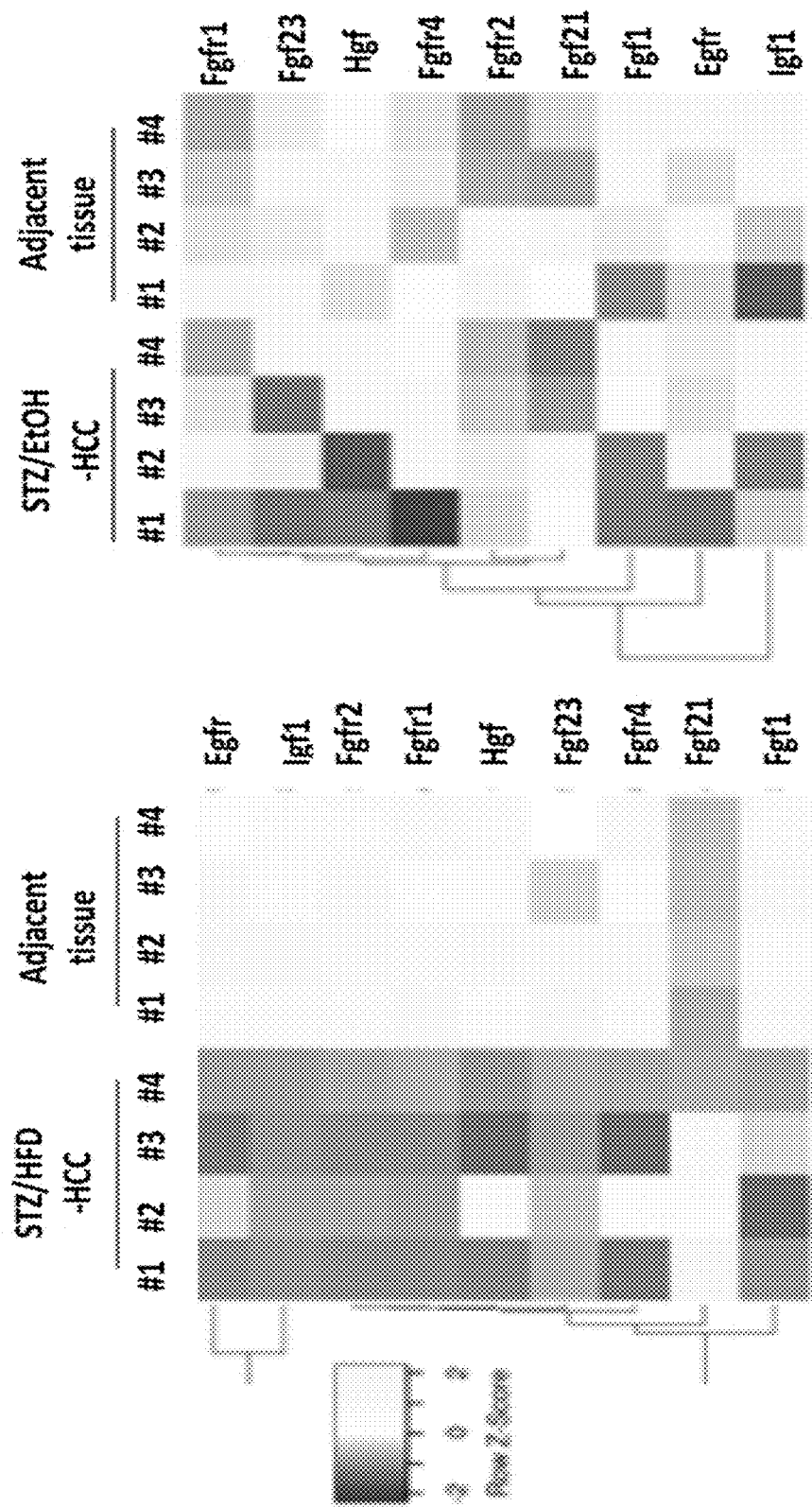
FIG. 8. Heatmaps for growth hormones and their receptors in NASH-associated HCC caused by STZ/HFD treatment (left) and ASH-associated HCC caused by STZ/alcohol treatment (right).

Example 5. Downregulation of Growth Hormones and Inhibition of Ras Pathways are Found in NASH-Associated HCC Induced by STZ and HFD Treatment but not in ASH-Associated HCC Caused by STZ and Alcohol Exposure Rat sarcoma (Ras) is a critical regulator for HCC development. Opposing signaling pathways triggered by Ha-ras- and β-catenin-dependent factors have been shown based on comparisons of expression patterns of periportal and peri-central hepatocytes with those of liver tumors carrying activating mutations in either the Ha-ras or the ctnnb1 gene.[38-40] Given our observations of activation of Wnt/β-catenin signaling in NASH-associated HCC in diabetic mice that received STZ and HFD administration, we expected that this type of tumor had decreased Ras activity. Indeed, downregulation of thirty-five Ras target genes and upregulation of the inhibitor of Ras signaling histidine phosphatase (Lhpp) were observed in NASH-associated HCC of the STZ/HFD treated livers. Growth hormones such as hepatocyte growth factor (Hgf) have been shown to induce Ras. Consistent with this observation, altered levels of Hgf, insulin-like growth factor (Igf)1, fibroblast growth factor (fgf)23, and fibroblast growth factor (fgf)21 were observed (FIG. 8 left). Inhibited expressions of receptors including fgfr1, fgfr2, fgfr4, and epidermal growth factor receptor (Egfr) were also detected (FIG. 8 left). However, no changes of the majority of these growth hormones and receptors were found except for the upregulation of Fgfr2 (FIG. 8 right).

These observations indicated that activation of the Wnt/β-catenin signaling but not Ras pathways in pericentral hepatocytes contributed to NASH to HCC development in diabetic livers during STZ and HFD treatment. In contrast, ASH-associated tumorigenesis had different mechanisms that did not involve Wnt/β-catenin and Ras pathways.

Heat maps showed low Ras activity and downregulation of growth hormones and their receptors in NASH-associated HCC caused by STZ/HFD treatment but not in ASH-associated HCC caused by STZ/alcohol treatment (FIG. 8).

Example 6. Differential Downregulation of Gluconeogenesis in NASH and ASH-Associated HCC Gluconeogenesis occurs in liver periportal zones and involves four irreversible steps catalyzed by the enzymes: pyruvate carboxylase (PC), phosphoenolpyruvate carboxykinase (Pck), fructose 1,6-bisphosphatase (Fbp), and glucose 6-phosphatase (G6pc). In the mammalian liver, PCK1 accounts for over 95% of gluconeogenesis activity. In human HCC samples, the expression levels of PCK and other key gluconeogenic enzymes are strikingly suppressed.[36] As expected, NASH and ASH-associated HCC show inhibition of gluconeogenesis in diabetic mouse livers as evidenced by transcriptional differential levels of G6pc, Fbp1, and Pck1 genes, which encode key enzymes in gluconeogenesis. Moreover, the transcriptional coactivator PGC-1α or Ppargc1a (peroxisome proliferative activated receptor, gamma, coactivator 1 alpha) is the primary regulator of liver gluconeogenesis, inducing increased gene expression for gluconeogenesis. Downregulation of Ppargc1a mRNA and protein were found in the STZ/HFD-induced tumors but not STZ/alcohol-induced HCC. These results indicated that more inhibition of gluconeogenesis was found in the NASH-associated HCC caused by STZ and HFD in comparison to ASH-associated HCC induced by STZ and alcohol. These findings regarding downregulation of gluconeogenetic enzymes were confirmed in Western analysis and IHC for Pck1.

TABLE 5

NASH-associated HCC caused by STZ and HFD showed greater downregulation of the gluconeogenesis pathway than ASH-associated HCC caused by STZ and alcohol. Fold change in log10 (LogFC) of mRNAs of gluconeogenetic genes or regulators from RNA Seq data. Significantly downregulated genes are in bold.

| Zone | Gene in gluconeo-genesis | STZ/HFD vs. adjacent tissue LogFC | P value | STZ/EtOH vs. adjacent tissue LogFC | P value |
|---|---|---|---|---|---|
| periportal | G6pc | −1.4604287 | 0.01335606 | −1.3504361 | 0.02048831 |
| periportal | Fbp1 | −1.775606 | 5.77E−05 | −0.8225474 | 0.02559728 |
| periportal | Pck1 | −2.9142315 | 0.00016403 | −1.5055727 | 0.02035734 |
| periportal | Ppargc1a | −1.2731358 | 0.00388098 | −0.7564803 | 0.06559875 |

Figure 9:
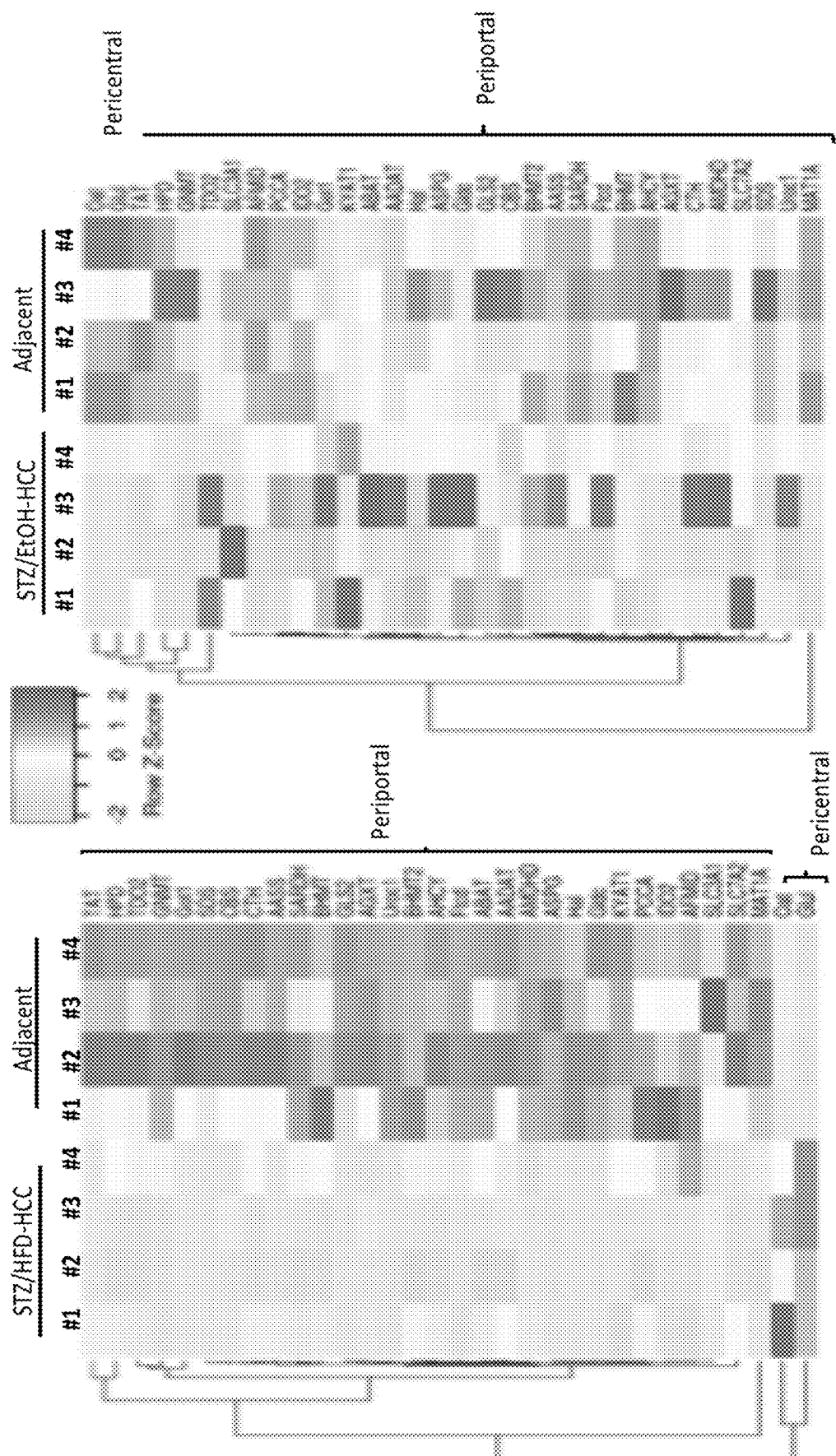
FIG. 9. Downregulation of periportal enzymes and upregulation of pericentral enzymes in amino acid metabolism during NASH to HCC development in the STZ/HFD treatment, whereas ASH to HCC progression had downregulation of enzymes in pericental zones.

Example 7. NASH and ASH-Associated HCC Exhibit Distinct Patterns of Zonation-Specific Enzymes in Amino Acid Metabolism Including Histidine Degradation Pathway Histidine is degraded to formiminoglutamic acid via three enzymes HAL, UROC1, and AMDHD1. Formiminoglutamic acid is further converted to formimino-THF by FTCD. These enzymes in histidine degradation are all carried out in the periportal zones. We found downregulation of genes HAL, UROC1, AMDHD1, and FTCD (Table 6) in NASH-associated HCC induced by STZ/HFD treatment whereas no change was found in ASH-associated HCC caused by STZ/alcohol treatment. Distinct patterns of zonation-specific enzymes in other amino acid metabolism were also observed. As shown in FIG. 9, almost all of the enzymes were downregulated in periportal zones (PP) (green color) whereas some enzymes including Glu1 (glutamine synthetase) at pericentral zones (PC) were upregulated in NASH associated HCC by STZ/HFD treatment (FIG. 9 left). In contrast, ASH-associated tumors had downregulation of enzymes in PC zones whereas enzymes in PP zones had mosaic induction patterns (FIG. 9 right). The Glu1 gene is critical for ammonia utilization and glutamine synthesis in pericentral hepatocytes. These results indicated between distinct patterns of zonation-specific enzymes in amino acid metabolisms in STZ/HFD- and STZ/EtOH-induced HCC.

TABLE 6

Downregulation of histidine degradation pathway in NASH associated HCC by STZ/HFD treatment and ASH associated HCC by STZ/alcohol.

| Zone | Gene in histidine degradation | STZ/HFD vs. adjacent tissue LogFC | P value | STZ/EtOH vs. adjacent tissue LogFC | P value |
|---|---|---|---|---|---|
| periportal | FTCD | −2.96 | $6.29 \times 10^{-6}$ | −0.00127 | 0.998 |
| periportal | AMDHD1 | −2.27 | $3.85 \times 10^{-4}$ | −0.0151 | 0.976 |
| periportal | UROC1 | −4.09 | $3.55 \times 10^{-6}$ | −0.164 | 0.775 |
| periportal | HAL | −5.38 | $8.84 \times 10^{-7}$ | −0.423 | 0.443 |

Example 8. NASH-Associated HCC Show Greater Inhibition of Periportal Genes in Urea Cycle than ASH-Associated HCC in Diabetic Mice Urea cycle occurs in periportal zones and has been shown to be altered in the STZ/HFD-induced tumors. Consistent with this previous report, downregulation of genes in urea cycle was seen in STZ/HFD-induced HCC (Table 7). In contrast, urea cycle did not change very much in ASH-associated HCC caused by STZ and alcohol, indicating differential alteration of urea cycle in the two types of tumors.

TABLE 7

NASH-associated HCC show greater inhibition of genes in urea cycle than ASH-associated HCC in diabetic mouse livers: expression patterns of genes in urea cycle in NASH or ASH-associated HCC from STZ/HFD or STZ/alcohol treatment in comparison to their corresponding adjacent tissues

| Zone | Gene in Urea Cycle | STZ/HFD vs. adjacent tissue | | STZ/EtOH vs. adjacent tissue | |
|---|---|---|---|---|---|
| | | LogFC | P value | LogFC | P value |
| Periportal | NAGS | −0.0004868 | 0.99733204 | −0.2345552 | 0.1190878 |
| Periportal | Cps1 | −5.1417192 | $9.68 \times 10^{-5}$ | −1.1275398 | 0.2227754 |
| Periportal | OTC | −2.2402136 | 0.00213352 | −0.9910269 | 0.12095288 |
| Periportal | ORNT1/Slc25a15 | −1.5094496 | 0.00180592 | −0.6857809 | 0.11150932 |
| Periportal | ARG1 | −5.2111744 | $2.85 \times 10^{-6}$ | −0.3507664 | 0.60806844 |
| Periportal | Citrin/Slc25a12 | −0.5998754 | 0.01862946 | −0.8981941 | 0.00108852 |
| Periportal | Ass1 | −3.6280434 | $1.27 \times 10^{-4}$ | −1.2853671 | 0.08093745 |
| Periportal | ASL | −2.9443906 | $1.84 \times 10^{-6}$ | −1.0850119 | 0.01648975 |

Example 9. ASH-Associated HCC Show Greater Inhibition of Pericentral Genes in Phosphatidylcholine Metabolism than ASH-Associated HCC in Diabetic Mice Phosphatidylethanolamine N-methyltransferase (PEMT) controls phosphatidylcholine metabolism, which takes place in pericentral zones. This enzyme converts phosphatidylethanol-amine into phosphatidylcholine, using S-adenosylmethionine (SAM-e) as a methyl group donor. This enzyme is crucial for maintaining liver choline levels. Although no change of PEMT gene was found in the NASH-associated HCC caused by STZ and HFD treatment, this gene was significantly downregulated in ASH-associated HCC caused by STZ and alcohol administration (Table 8).

TABLE 8

Greater inhibition of genes of phosphatidylcholine metabolism in ASH-associated HCC than NASH-associated tumors in diabetic mouse livers.

| Zone | Gene in phosphatidylcholine metabolism | STZ/HFD vs. adjacent tissue | | STZ/EtOH vs. adjacent tissue | |
|---|---|---|---|---|---|
| | | LogFC | P value | LogFC | P value |
| pericentral | PEMT | −0.1891974 | 0.65108596 | −1.1790754 | 0.01056976 |

Figure 10:
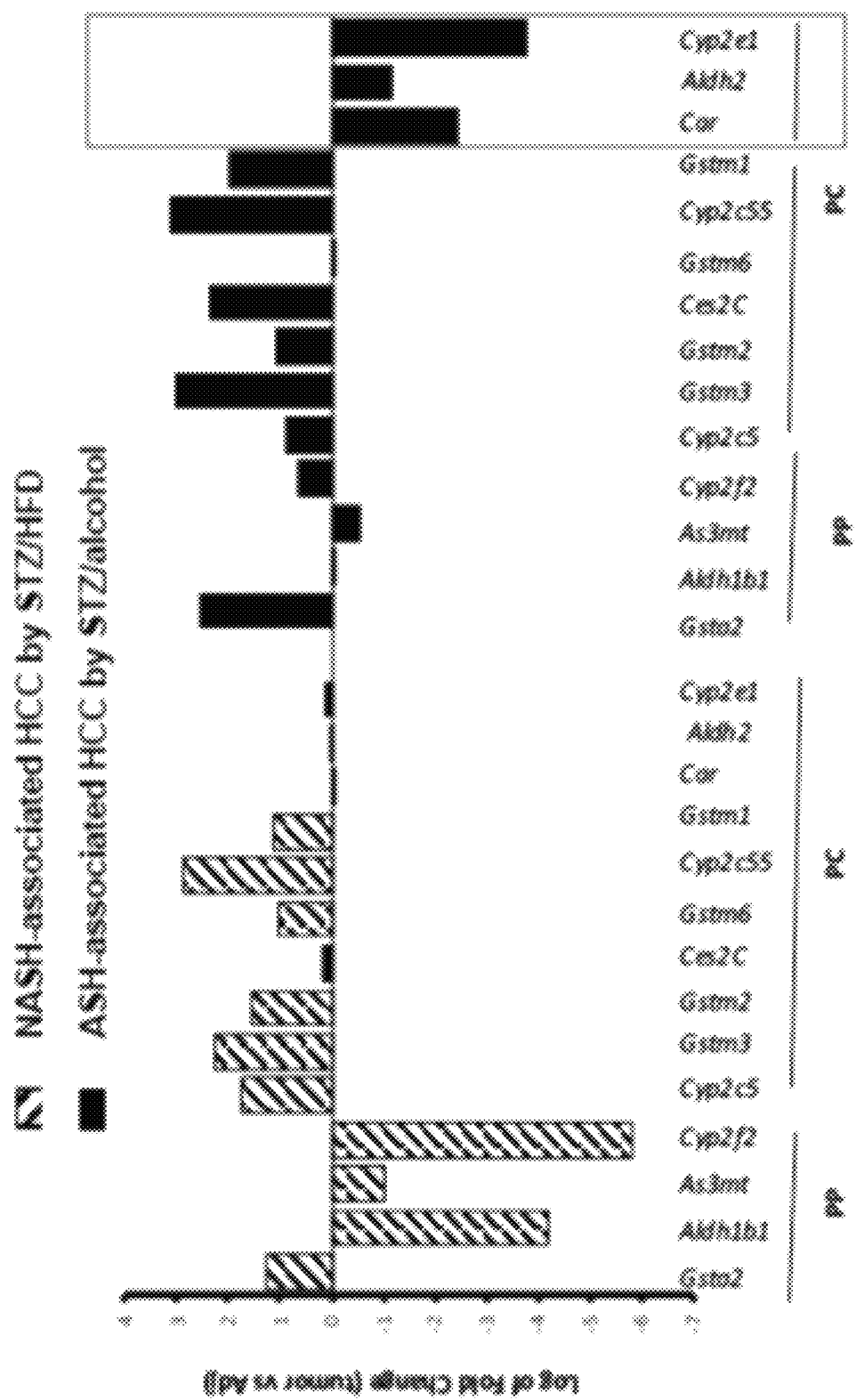
FIG. 10. Different expression patterns of detoxification in periportal (PP) and pericentral (PC) zones of NASH and ASH-associated HCC induced by STZ/HFD and STZ/alcohol protocols, respectively.

Example 10. NASH and ASH-Associated HCC Exhibit Distinct Patterns of Zonation-Specific Enzymes of Xenobiotics Metabolism in Diabetic Mouse Livers Different expressions of detoxification enzymes between STZ/HFD- and STZ/alcohol-induced HCC were also observed (FIG. 10. Many detoxification enzymes in periportal zones were downregulated whereas many enzymes in pericentral zones were upregulated during NASH to HCC development in the STZ/HF treatment. In contrast, upregulation of many periportal enzymes was seen during ASH to HCC progression whereas multiple pericentral specific genes Car, Aldh2, and Cyp2E1, which encode key regulators and enzymes for detoxification of alcohol, were downregulated.

Example 11. ASH-Associated HCC Exhibit Significantly More Inhibition of Bile Acid Synthesis than NASH-Associated HCC in Diabetic Mouse Livers The conversion of cholesterol to bile acids occurs in pericentral zones of the liver and is mediated by two bile acid synthesis pathways. The classic pathway is initiated by cholesterol 7α-hydroxylase (CYP7A1) and the alternative pathway is initiated by steroid 27-hydroxylase (CYP27A1). 3β-hydroxysteroid dehydrogenase (3β-HSD) converts 7α-hydroxycholesterol to 7α-hydroxy-4-cholesten-3-one (C4). A branch enzyme Sterol 12-hydroxylase (CYP8B1) synthesizes cholic acid (CA). Without 12α-hydroxylation, chenodeoxycholic acid (CDCA) is synthesized. Mitochondrial CYP27A1 catalyzes oxidation of the steroid side chain, and the peroxisomal β-oxidation reaction cleaves a 3C unit to form C24 cholestenoic acid, the backbone of most bile acids. CDCA is converted to α- and β-muricholic acids (α-MCA and β-MCA, respectively) in mouse livers. Bile acids are immediately conjugated to the amino acids taurine or glycine (TCA or TCDCA, respectively) for secretion into bile. In addition, Slc27a5 encodes bile acyl-CoA synthetase capable of activating very long-chain fatty-acids containing 24- and 26-carbons. Its primary role is in fatty acid elongation or complex lipid synthesis rather than in degradation. Sterol carrier protein 2 (Scp2) encodes non-specific lipid-transfer protein involved in lipid metabolism, and may play a role in Zellweger syndrome in which cells have impaired bile acid synthesis. ACOX2 encodes a peroxisomal enzyme that oxidizes CoA esters of bile acid intermediates and branched fatty acids. We compared levels of genes in bile acid pathways in NASH and ASH-associated HCC. As listed in the Table 9, only Cyp7b1 and Cyp8b1 were inhibited in the NASH-associated HCC after STZ and HFD administration. In contrast, Cyp7a1, Cyp27a1, 3β-HSD, Cyp8b1, Slc27a5, and Scp2 were significantly downregulated whereas Acox2 was upregulated in the ASH-associated HCC caused by STZ and alcohol treatment. These observations suggested greater alteration of bile acid synthesis in ASH-associated HCC than NASH-associated tumors in diabetic mouse livers.

TABLE 9

ASH-associated HCC caused by STZ/alcohol treatment show greater alteration of bile acid synthesis than NASH-associated HCC caused by STZ/HFD administration: expression levels of related genes from RNA Seq data. (Downregulated and upregulated genes were highlighted in bold.)

| Zone | Bile acid synthesis | STZ/HFD vs. adjacent tissue LogFC | P value | STZ/EtOH vs. adjacent tissue LogFC | P value |
|---|---|---|---|---|---|
| Pericentral | Cyp7a1 | −0.2820409 | 0.73910579 | −3.7169274 | 0.00073788 |
| Pericentral | Cyp7b1 | −2.1723367 | 0.00196524 | −0.6648159 | 0.2711769 |
| Pericentral | Cyp8b1 | −3.7735505 | 0.0083087 | −2.6212141 | 0.04451128 |
| Pericentral | Hsd3b7 | 0.36131586 | 0.09152857 | −1.0055791 | 0.00010483 |
| Pericentral | Akr1d1 | −0.6789762 | 0.16774627 | −0.7173981 | 0.14608424 |
| Pericentral | Cyp27a1 | −0.1958807 | 0.59539487 | −1.48212481 | 0.00072383 |
| Pericentral | Slc27a2 | −0.7879692 | 0.02218233 | −0.8531451 | 0.01435354 |
| Pericentral | Slc27a5 | −0.6907458 | 0.07607522 | −1.1144527 | 0.00717887 |
| Pericentral | Amacr | 0.3175463 | 0.23923649 | −0.8344183 | 0.00491799 |
| Pericentral | Acox2 | −0.013033 | 0.96979604 | 1.1379025 | 0.00358828 |
| Pericentral | H5d17b4 | −0.1732011 | 0.57841568 | −0.1209878 | 0.69726716 |
| Pericentral | Scp2 | −0.6238773 | 0.08102989 | −1.1813477 | 0.00258116 |
| Pericentral | baat | −0.9936861 | 0.03357498 | −0.4827591 | 0.27677453 |

Figure 15:
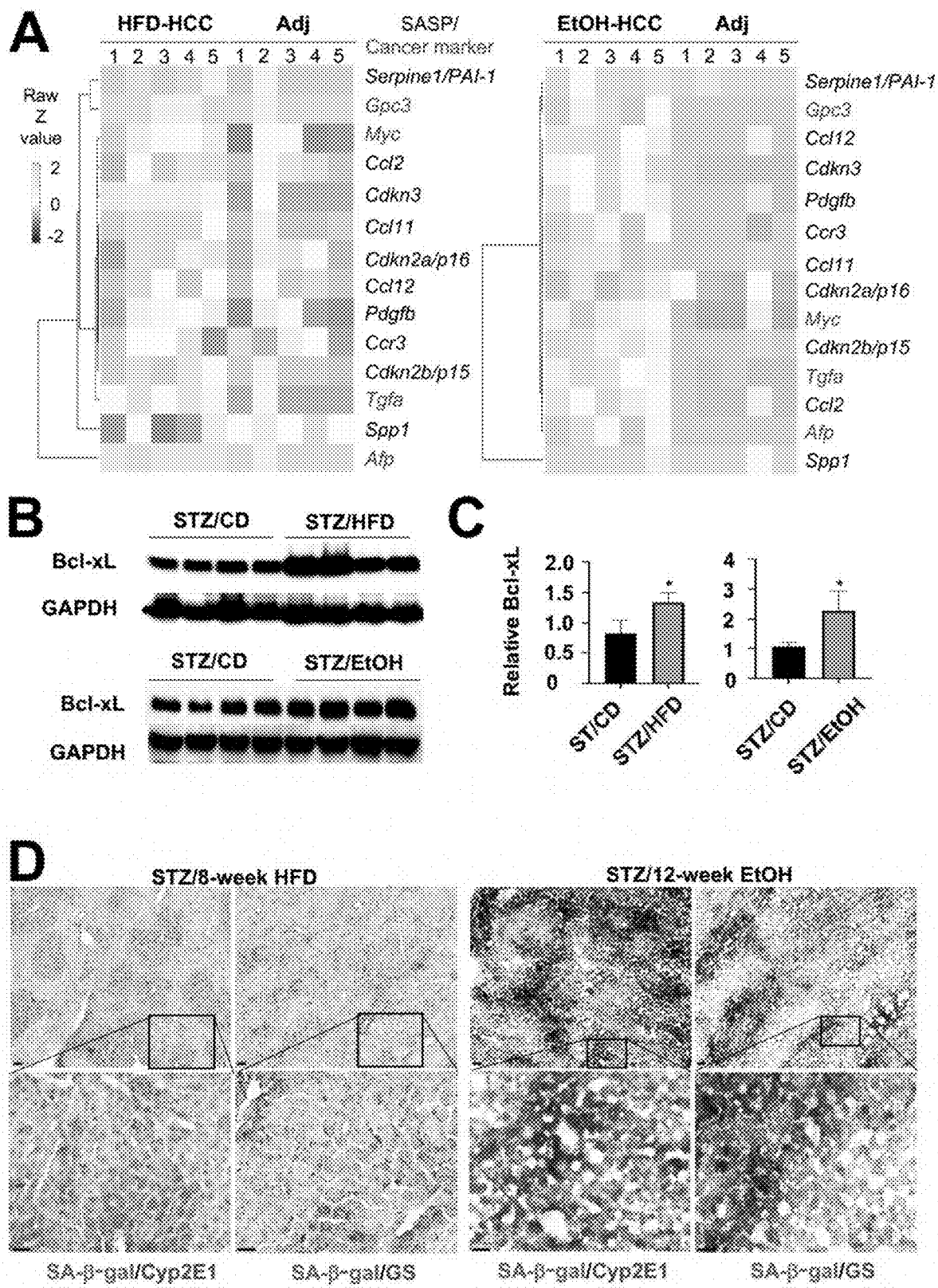
FIG. 15. HFD-associated hepatocarcinogenesis is associated with periportal senescence, whereas EtOH exposure causes extensive pericentral senescence with accumulation of Bcl-xL protein in diabetic livers. (A) Heatmaps illustrated greater association of liver cancer markers with senescence-related factors in EtOH-HCC than HFD-HCC (n=5 per group). Western blotting. (B and C) Bcl-xL was accumulated during HFD- and EtOH-associated hepatocarcinogenesis in Western blotting (B) and densitometric quantification (C). Data were means±SD from four animals per group. *P<0.05, (D) IHC for SA-β-gal and pericentral markers GS and Cyp2E1 detected periportal senescence in STZ-treated liver after 8-week HFD feeding and pericentral senescence in STZ-treated liver after 12-week EtOH exposure.

Example 12. Distinct Zonation-Specific Patterns of Hepatic Senescence During HFD and EtOH-Induced Hepatocarcinogenesis Cellular senescence has been implicated in the etiology of chronic liver diseases including cirrhosis and HCC. Heatmaps in EtOH-induced HCC revealed upregulation of genes involved in senescence associated secretory phenotype (SASP), including plasminogen activator inhibitor 1 (Serpine1/PAI-1), C-C Motif Chemokine Ligand (Ccl)2, Ccl11, Ccl12, Cyclin Dependent Kinase Inhibitor (Cdkn)3, platelet derived growth factor (Pdgn-b, C-C Motif Chemokine receptor (Ccr)3, Cdkn2a/p16, Cdkn2b/p15, and Secreted Phosphoprotein (Spp)1, along with oncogenic genes Myc and transforming growth factor (Tea, and liver cancer markers Gpc3 and Afp. In contrast, few SASP genes were upregulated in HFD-induced tumors (FIG. 15A). The antiapoptotic Bcl-xL is a modulator of senescence.[7] High expression of BCL2L1 (the gene encoding BCL-XL) in human HCC has been previously shown.[13,54] Consistent with these findings, induced levels of Bcl-xL protein were found in the diabetic livers after 90-day HFD feeding or 180-day ethanol exposure in comparison to controls that were fed normal chow (FIGS. 15B and C). Thus, induction of Bcl-xL protein was a common mechanism during both HFD and ethanol-induced HCC development.

To further understand cellular sources of senescence during HFD and EtOH-induced hepatocarcinogenesis, we histologically analyzed the diabetic murine livers that were fed HFD for 90 days or ethanol for 180 days. Considering that senescent cells express an increased level of lysosomal senescence associated-β-galactosidase activity (SA-β-gal), we performed X-staining in combination with IHC for pericentral hepatocyte markers Cyp2E1 or glutamine synthetase (GS), a product of Glul gene. Metabolism of HFD in the diabetic murine livers was associated with senescence in periportal zones that were negative for staining with Cyp2E1 and GS antibodies (FIG. 15D, left panels). In contrast, cell senescence in the STZ-treated livers after ethanol exposure mainly occurred in pericentral hepatocytes that were damaged due to metabolism of this chemical (FIG. 15D, right panels). These results indicated that periportal hepatocytes became senescent due to dysregulation of metabolism after HFD feeding, whereas pericentral hepatocytes were senescent after chronic ethanol exposure in livers under diabetic conditions.

Figure 16:
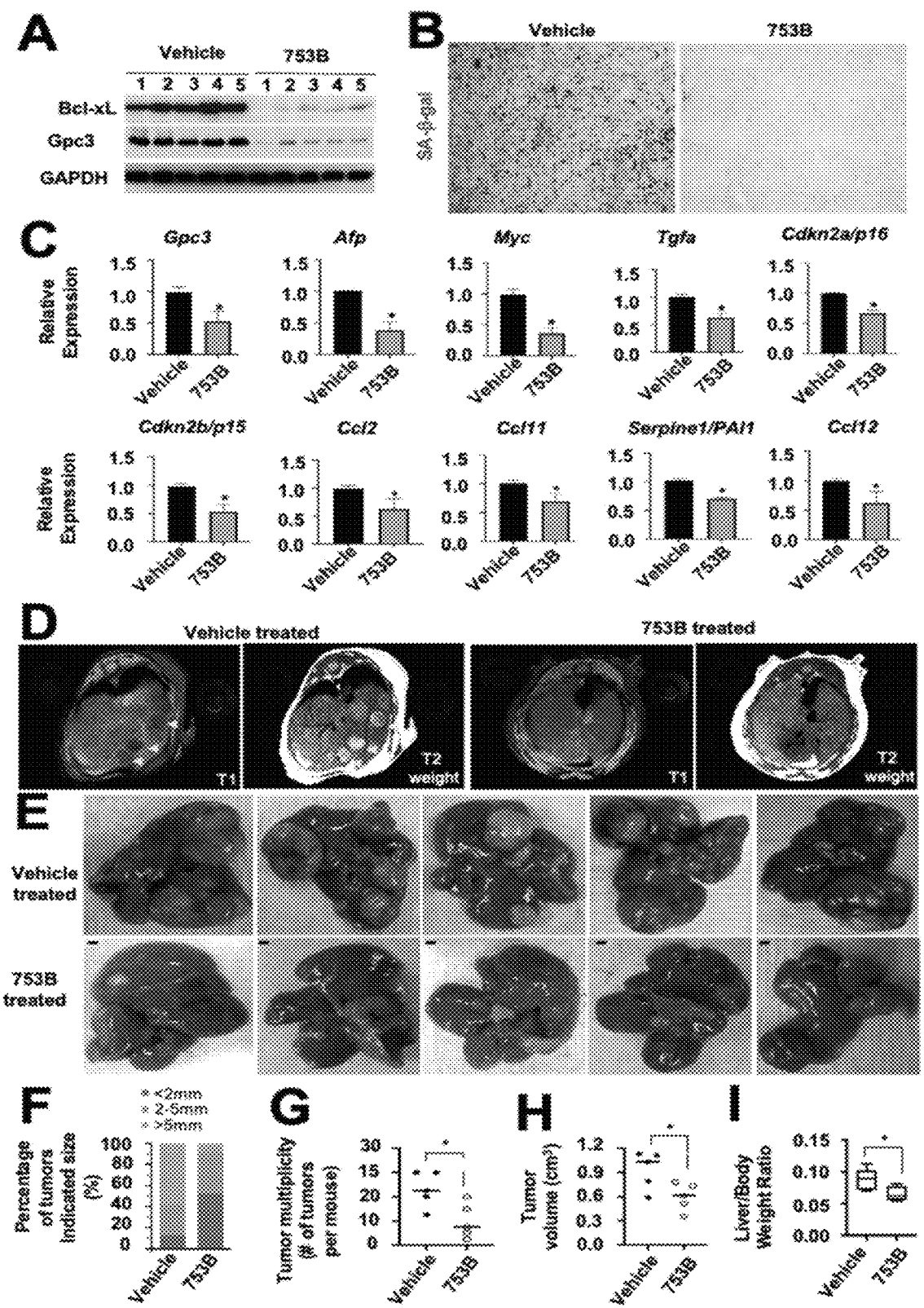
FIG. 16. The senolytic Bcl-xL and Bcl-2 dual PROTAC 753B clears up senescent cells and inhibits EtOH-HCC. (A) Western blotting showed that 6-month 753B administration inhibited Bcl-xL accumulation and blocked induction of the liver cancer marker Gpc3 protein in STZ/EtOH-treated livers, whereas Vehicle controls did not. (B) X-gal staining for SA-β-galactosidase activity showed that 753B administration inhibited senescent cell accumulation in the STZ/EtOH-treated livers. Scale bar: 150 mm: (C) Q-RT-PCR detected that 753B administration inhibited mRNA levels of senescence and liver cancer markers. Data were means±SD of triplicate experiments. *P<0.05. (D) Representative MRI imaging demonstrated determination of tumor lesions (indicated by arrows) based on hypointense signals in T1 but hyperintense signals in T2-weighted image. (E) Morphological overview of EtOH-HCC occurrence in livers that were exposed to 6-month 753B (lower images) or Vehicle (upper images). (F-I) Quantification of tumor size (F), tumor number (G), tumor volume (Hi), ratio between liver and body weight (I) in the STZ/EtOH-treated livers after 6-month 753B administration. Values were expressed as means±SD from 5 mice per group. *P<0.05.

Example 13. The Senolytic Bcl-xL and Bcl-2 Dual PROTAC 753B Clears Up Senescence and Inhibits Etoh-HCC PROTACs are bivalent small molecules containing a ligand that recognizes a target protein linked to another ligand that recruits a specific E3 ubiquitin ligase.[46,47] PROTAC binding induces proximity-induced ubiquitination of the target protein and its subsequent degradation by proteasomes. PROTACs act catalytically to induce protein degradation in a sub-stoichiometric manner. They result in less drug exposure and reduced toxicity compared with traditional inhibitors since their effect is not limited by equilibrium occupancy. Because of their improved and prolonged activity profile, they are increasingly used to develop more effective antitumor agents and other therapeutics.[48-50] Importantly, because PROTACs rely on E3 ligases to induce protein degradation, it is possible to achieve cell/tissue selectivity, even when the target proteins are ubiquitously expressed as long as they target the proteins to an E3 ligase that is cell- or tissue-specific. PROTAC technology was used to develop a Bcl-xL specific PROTAC (Bcl-xL-P), which targets Bcl-xL to the E3 ligase cereblon (CRBN) or VHL. ES ligases cereblon and VHL are poorly expressed in platelets.[51-53] Bcl-xL and Bcl-2 dual PROTACs/degraders that link to the VHL ligand and target Bcl-xL and Bcl-2 to VHL for ubiquitination and proteasome degradation were also developed. These Bcl-xL and Bcl-2 dual PROTACs/degraders are not only potent antitumor agents but also effective senolytic agents. PROTAC 753B targets Bcl-xL and Bcl-2 for proteasome degradation by linking to E3 ligase VHL. 753B had a high senolytic activity in livers of aging and STZ/HFD-treated mice (data not shown). We examined the effect of 753B on EtOH-induced hepatocarcinogenesis. 753B was administered through intraperitoneal injection at 5 mg/kg body weight every other day starting at one week after alcohol consumption. In parallel experiments, vehicle-treated control animals received a compound that could not interact with the VHL E3 ligase. Five-month administration of 753B effectively inhibited Bcl-xL accumulation and reduced Gpc3 expression in the diabetic livers that were exposed to 6-month feeding of 5% ethanol (FIG. 16A). Measurement of the SA-β-gal activity by X-gal staining indicated little senescence in the 753B/EtOH-treated diabetic livers compared to Vehicle-treated controls (FIG. 16B). Moreover, we detected significant reduction of SASP genes (Cdkn2a/p16, Cdkn2b/p15, Ccl2, Ccl11, Serpine1/PAI1, Ccl12), liver cancer markers (Gpc3 and Afp), and oncogenes (Myc, and Tgfa) at mRNA levels in the 753B/EtOH-treated diabetic livers compared to Vehicle-treated controls by Q-RT-PCR analysis (FIG. 16C). Magnetic resonance imaging (MRI) can allow precise and accurate quantification of tumour volume. Therefore, we performed abdominal MIll examinations before or after Gd-chelate-enhanced MRI. HCC lesions were identified based on hypointense signals in T1 and hyperintense signals in T2-weighted scan at 6 months after EtOH feeding in the diabetic murine livers. In contract few lesions were found in EtOH fed animals treated with 753B (FIG. 16D). These MIll signals matched morphological evaluations of liver cancers in the sacrificed animals (FIG. 16E). Morphological evaluation of tumor diameter demonstrated that 58.7% tumors were >5 mm in size, 29% were 2-5 mm, and 12.3% were <2 mm in control livers, whereas the majority of tumors in 753B-treated livers were small in size (<2 mM and 2-5 mm) (FIG. 16F). Quantitative data indicated that the 753B administration efficiently inhibited formation of tumor nodules in number and volume (FIGS. 16G and H). Ratio of liver to body weight is an indicator of hepatocyte proliferation during liver regeneration and liver cancer development. 753B administration significantly decreased the ratio of liver to body weight (FIG. 16I). Taken together, these data indicated that 753B degraded Bcl-xL, effectively cleared senescent cells, and blocked EtOH-associated hepatocarcinogenesis. Therefore, 753B was shown to be effective in preventing or reducing the severity of EtOH-associated hepatocarcinogenesis.

Figure 17:
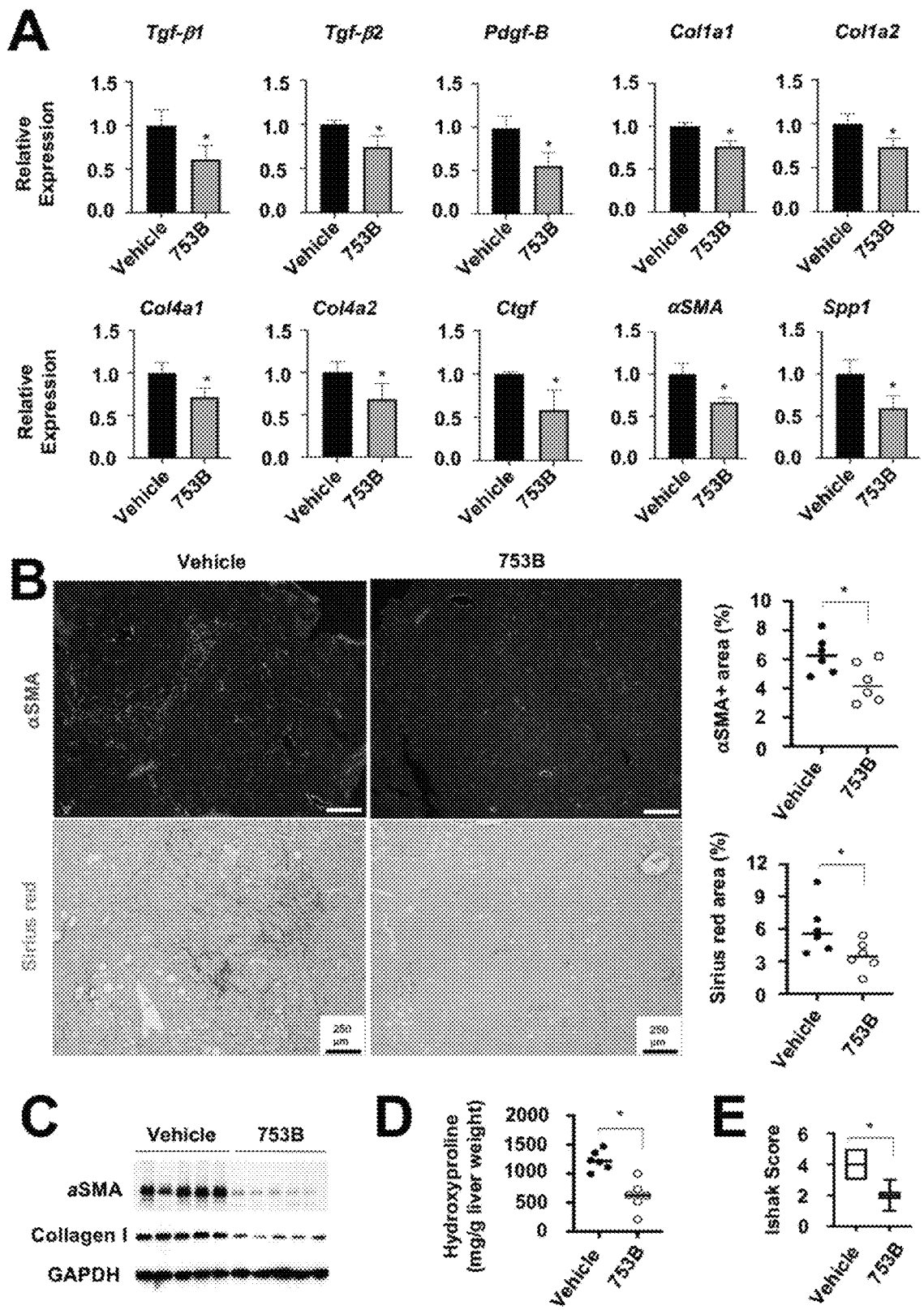
FIG. 17. 753B administration inhibits myofibroblast cell activation and liver fibrosis during EtOH-associated hepatocarcinogenesis. (A) Q-RT-PCR analysis detected lower levels of fibrosis-related genes in livers of STZ/HFD-treated mice that received 6-month 753B administration in comparison to controls. Data were means±SD of triplicate experiments. *P<0.05. (B) Immunofluorescent staining for aSMA and Sirius red staining for collagen fibril indicated that 753B administration attenuated liver fibrosis as evidenced by few myofibroblast activation and little collagen deposition in the STZ/HFD-treated livers. Positive staining areas were quantified from staining of 6 mice per group by Image J software. Data were expressed as means±SEM. *P<0.05. Scale bar: 200 mm. (C) Western blotting detected low levels of aSMA and pro-collagen type I proteins in the STZ/EtOH/753B-treated livers. (D and E) Hepatic hydroxyproline assay (D) and Ishak Scores (E) confirmed lower levels of collagen and liver fibrosis in the STZ/EtOH/753B-administered livers than controls. Quantification was performed from 5-6 livers per group and was expressed as means±SEM. *P<0.05.

Example 14. 753B Administration Inhibits Myofibroblast Cell Activation and Liver Fibrosis During EtOH-Associated Hepatocarcinogenesis Fibrosis is characterized by myofibroblast cell activation and excessive collagen deposition. Extensive fibrotic reaction has been reported during NASH to HCC transition through the chemical and dietary intervention by STZ/HFD cotreatment.[4] We compared effects of 753B and control compound on liver fibrosis in the diabetic animals after 5-month drug administration. Q-RT-PCR analysis detected significant downregulation of several fibrosis-related markers including alpha-smooth muscle actin (aSMA), pro-collagen (Col)1a1, Col1a2, Col4a1, Col4a2, transforming growth factor (Tgf)-b2, connective tissue growth factor (Ctgf), platelet-derived growth factor (Pdgf)-b, and Spp1 in animals that received 753B administration (FIG. 17A). Moreover, 753B administration significantly reduced myofibroblast activation as revealed by immunofluorescent staining and Western blotting of aSMA (FIGS. 17B and C). Accordingly, collagen deposition was significantly lower in livers of 753B treated animals than those in controls as shown by Sirius red staining and Western analysis (FIGS. 17B and C). Decreased liver fibrosis was further verified after quantitative measurement of collagen content based on hydroxyproline assay in livers exposed to 753B administration (1031.8±116.4 versus 721.2±215.0) (FIG. 17D). Ishak score of the liver tissue in the livers were also analyzed. Grade 0 has no fibrosis. Grade 1 has fibrous expansion of some portal areas, with or without short fibrous septa. Grade 2 contains fibrous expansion of most portal areas, with or without short fibrous septa. Grade 3 has fibrous expansion of most portal areas with an occasional portal to portal bridging. Grade 4 contains fibrous expansion of portal areas with marked bridging including portal-portal and portal-central bridging. Grade 5 has marked portal-portal and portal-central bridging with occasional nodules (incomplete cirrhosis). Grade 6 has cirrhosis, probable or define. 753B administration significantly decreased Ishak score in comparison to controls (FIG. 17E). Collectively, these data show that 753B administration inhibited liver fibrosis characterized by attenuated extents of myofibroblast activation and collagen deposition.

Example 15. Discussion

Figure 11:
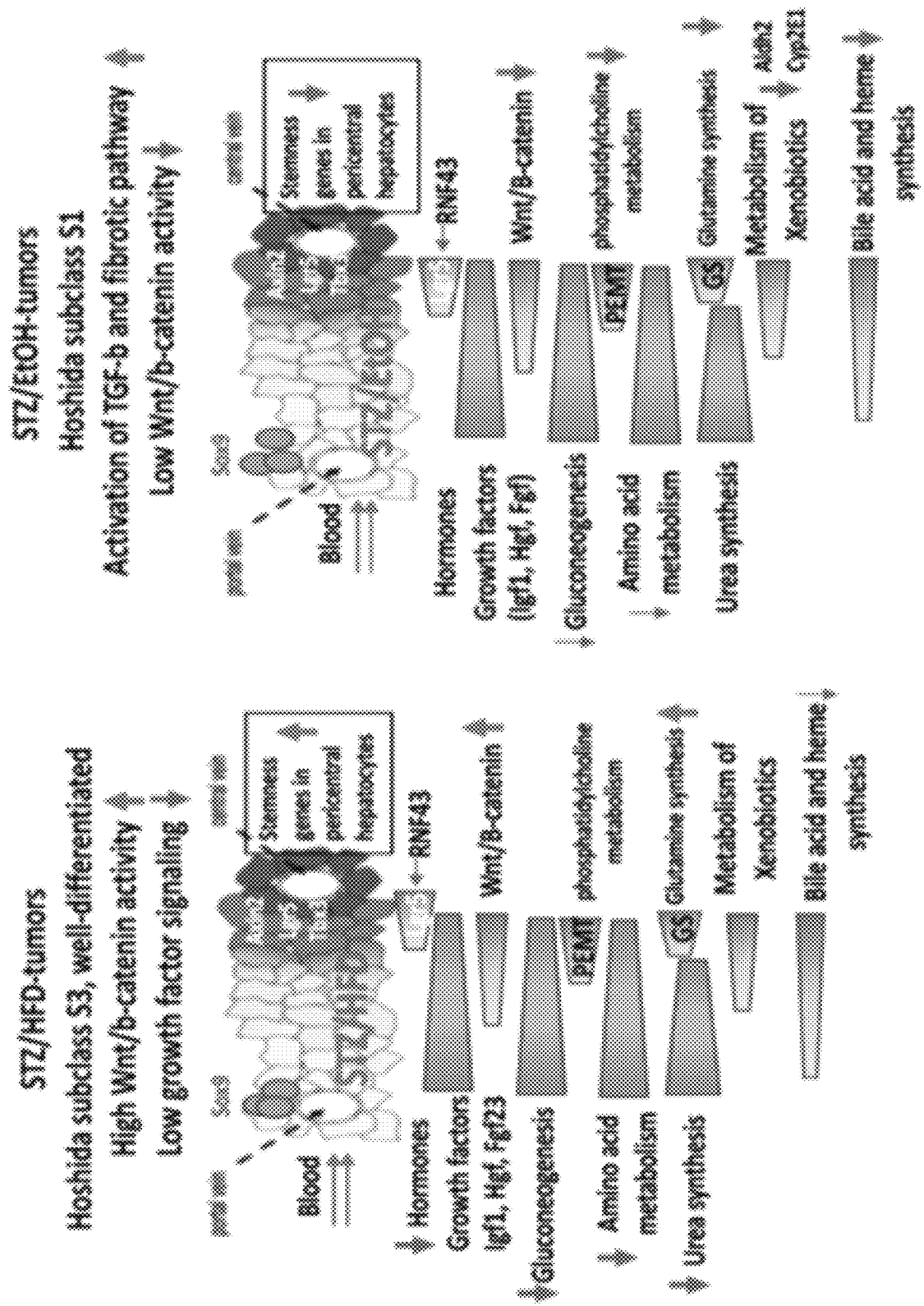
FIG. 11. Different molecular changes during NASH to HCC development by STZ/HFD treatment and ASH to HCC transition by STZ/alcohol treatment. Zonation-specific gradients in the molecular changes are indicated. High levels of periportal activities (right pointing trapezoids) and high pericentral activities (left pointing trapezoids) are shown. Down and up arrows indicate down-regulation and upregulation, respectively.
Figure 12:
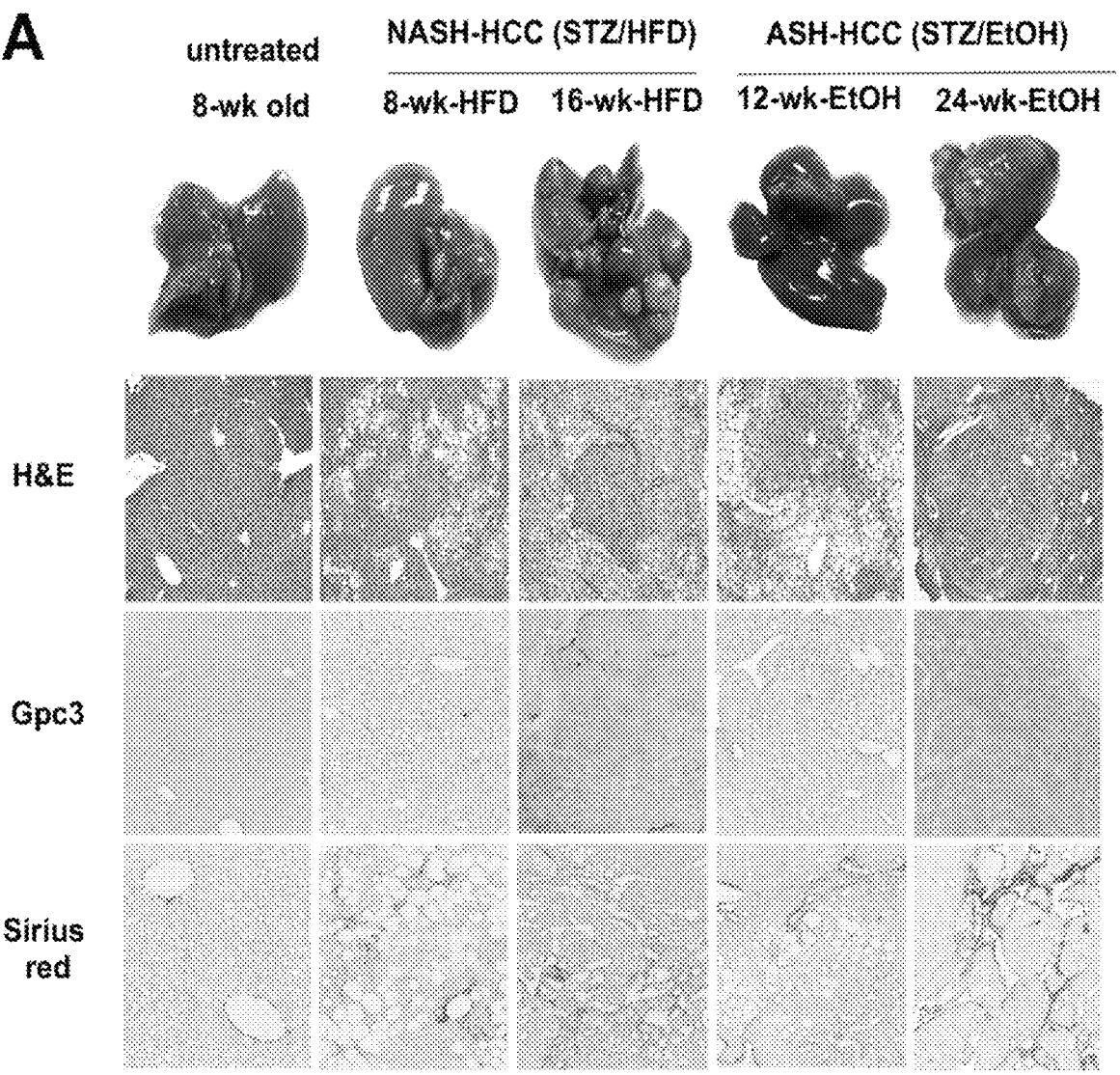
FIG. 12. Dietary interventions through chronic alcohol consumption or HFD feeding in combination with the diabetic inducer STZ cause common liver pathologies including steatohepatitis, fibrosis, and HCC in mice. Animals (n=23) received STZ at P2. HFD or EtOH feeding started at P30 (n=20) or P60 (n=20) respectively. (A) Morphological and histological characterizations of steatohepatitis, fibrosis, and HCC at indicated time points. Controls (n=3) were untreated at 24-wk old. Scale bar: 200 um. (B and C) Induction of hepatic Afp, and Gpc3 in HCC livers that received the feeding of 16-wk HFD or 24-wk EtOH were observed in qRT-PCR analysis (B) and Western blotting (C). Data are mean±SD from triplicate experiments. **P<0.01.
Figure 12:
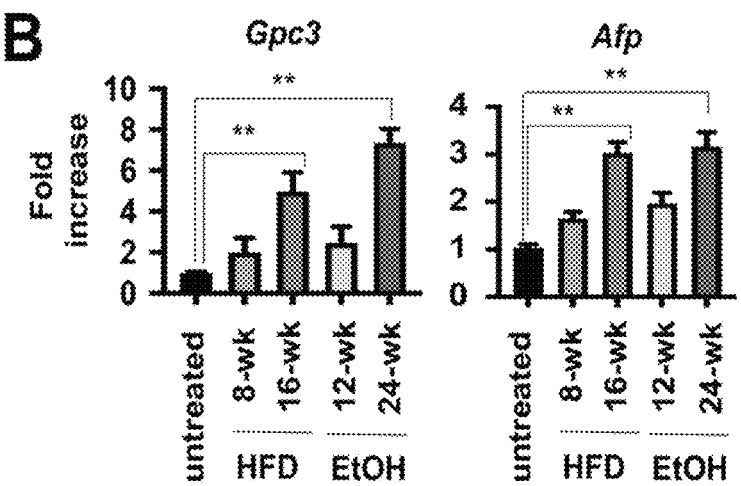
Figure 12:
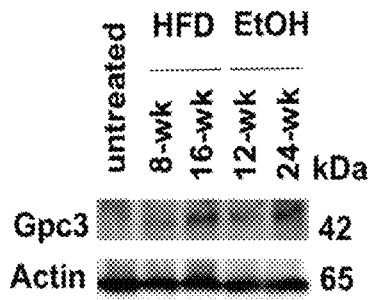

We have developed an ASH-HCC mouse model by combining STZ injection and alcohol administration. HCC development in NASH or ASH appear to have different mechanisms of metabolic reprogramming and stemness activation in livers of STZ-treated diabetic mice (FIG. 11). NASH-associated HCC caused by STZ/IIFD treatment resembles Hoshida subclass S3 of human liver cancer, are well-differentiated, express high Wnt/β-catenin activity, and show low growth factor signaling. The dominant role of Wnt/β-catenin signaling in governing metabolic zonation in the liver has been well established. This pathway is particularly involved in the regulation of pathways limited to or predominating in the pericentral zone such as glutamine synthesis, drug metabolism, bile acid, and heme synthesis. Upregulation of Wnt pathways regulators can be indicated by universal β-catenin target gene expression: Lgr5, Lef1, Ihh, Tbx3, Rnf43, and Axin2 as well as increased levels of glutamine synthesis. When β-catenin signaling is induced, periportal functions have been found to be down-regulated.[38,39] Consistent with these previous reports, NASH-associated HCC caused by STZ/HFD treatment had low levels of periportal-specific genes including growth hormones, gluconeogenesis, amino acid metabolism, and urea synthesis.

Metabolic reprogramming or "deregulating cellular energetics" is a hallmark of cancer. Metabolic zonation appeared to be altered differentially in the HFD-HCC and EtOH-HCC.

HFD-HCC was well-differentiated, pericentralized, and deperiportalized tumor type with upregulation of the Wnt/β-catenin targets but low Ras signaling. These features are similar to differentially expressed genes from liver tumors that harbor activating mutations in murine Catnb and human Ctnnb1.[43,44] Activation of the Wnt/β-catenin pathway seems to reprogram tumor cells towards an imbalanced nutrient uptake: choline and glutamine addition. Aberrant choline and lipid metabolism often occur in cancer cells and contribute to proliferative growth and programmed cell death. SCL22A3 encodes the transporter organic cation transporter 3 and its upregulation can promote uptake of choline. Glutamine is a key substrate required for anabolic growth of cells. It not only provides nitrogen for protein and nucleotide synthesis but also acts as a signal for mTORC1 activation and for uptake of essential amino acids to promote protein translation. Glutamine-dependent cancer cells undergo a dramatic metabolic reprogramming such that mitochondria are reprogrammed to produce anabolic precursors from glutamine.[45] Moreover, glutamine addition likely enables the tumor cell resistance to oxidative stress since glutamine stimulates the glutathione synthesis for antioxidant response.

In EtOH-HCC, we found downregulation of pericentral-specific genes for enzymes, receptors and other signal regulators, including PEMT, Cyp2E1, Glu1, Oat, Aldh2, Cpox, Ahr, and Rhbg. PEMT is expressed primarily in zone 3 and regulates a step in phosphatidylcholine metabolism for phospholipid synthesis. Cyp2E1 encodes members of cytochrome P450 enzymes (CYP) in pericentral zones that serve to detoxify xenobiotics before they are drained into the central vein. For compounds metabolically activated by CYPs, such as CC14, acetaminophen, and ethanol, the zonated expression causes a pericentral pattern of necrosis. The Glu1 gene encodes glutamine synthetase. A zonated metabolic pattern is also known for ammonia metabolism. Urea-cycle enzymes detoxify ammonia by high capacity and low affinity mechanisms in the periportal and midzonal regions. Low remaining ammonia concentrations are removed from the sinusoidal blood by a pericentral ring of glutamine synthetase positive hepatocytes that act by a low capacity, high affinity mechanism. Oat encodes ornithine aminotransferase, a key enzyme for conversion of arginine and ornithine into the major excitatory and inhibitory neurotransmitters glutamate and GABA. Aldh2 is a pericentral enzyme that detoxifies ethanol. Coproporphyrinogen oxidase (CPDX) is involved in heme biosynthesis. In addition, AhR (Aryl hydrocarbon receptor) is a pericentral gene. Ahr downregulation was only found in ASH-associated HCC (Log fold change: −1.393, P value: 0.000115) but not NASH-associated HCC in our diabetic mouse livers. Rhbg, an ammonia transporter protein in pericentral zones, was also downregulated only in ASH-associated HCC (Log fold change: −2.93, P value: 0.0014). Since all of these genes are transcriptionally regulated by the WNT/β-catenin pathway,[41,42] their downregulation indicated inhibitory effects of alcohol on stemness activation mediated by this pathway in the ASH-associated HCC of STZ-treated, diabetic mouse livers. Besides the low Wnt/β-catenin activity, our data suggests that the alcohol-induced HCC induced by STZ/alcohol treatment are similar to Hoshida subclass 51 of human liver cancer characterized by activation of TGF-β and fibrotic pathway, high P53 signature.

Bile acids are end products of cholesterol metabolism. They are synthesized in pericentral hepatocytes. Altered bile acid signaling in the liver is associated with severe diseases including the development of cholestasis and HCC.[58] Deficiency in bile salt export pump or bile acid receptor are associated with HCC.[59,60] Downregulation of genes in bile acid synthesis and phosphatidylcholine metabolism in our EtOH-HCC model is likely a result of a metabolic shift from β-oxidation due to the obliteration of healthy hepatocytes due to chronic ethanol exposure. Such damage is consistent with low Wnt/β-catenin signaling, reduced expression of ethanol detoxification enzymes Cyp2E1 and Aldh2, and pericentral senescence in this study. Despite of these abnormalities in pericentral hepatocytes, it takes more than 6 months for the development of EtOH-HCC. In contrast, HFD-HCC develops within 3-4 months in diabetic mice. The development of HCC with active Wnt/beta-catenin signaling in mice and human likely involves periportal senescence. In supporting this notion, a specific histologic pattern with intratumor cholestasis has been found in human HCC bearing Ctnnb1 mutation.[61] Collectively, HCC can result from pericentral or periportal senescence. They may have decreased or activated Wnt/β-catenin signaling based on the location of hepatocyte damage. These deregulations highlight importance of a balanced Wnt/β-catenin signaling for proper periportal and pericentral functions in liver homeostasis.

Senescent cells have recently emerged as therapeutic targets for age-related diseases including cancer. They play a causal role in many age-related diseases via expression of the SASP to secret various inflammatory mediators and proteases.[62-68] Small molecules that can selectively kill senescent cells, termed senolytics, have the potential to prevent and treat a growing number of age-related diseases and extend healthspan.[63,64] Inhibitors of the anti-apoptotic Bcl-2 family proteins are one type of senolytics.[69,70,71]

Persistent insults due to obesity and alcoholism can cause chronic inflammation leading to cycles of damage and renewal, irreversible scarring, and HCC. The development of NASH or ASH-associated HCC is a stepwise process and may take several decades to evolve into chronic conditions. It is difficult to follow changes of liver histology in patients due to the asymptomatic nature of NAFLD or ALD during early stages. Patients with liver function failure are often at advanced stages of the diseases, and therefore the only option for treatment is to carry out a liver transplantation. However, liver donors are limited every year. There is an urgent need to identify molecular targets and develop anti-fibrotic and anti-HCC therapy for the treatment of NAFLD and ALD. In this study, our intervention using STZ and alcohol feeding induced steatosis, ASH, liver fibrosis, and HCC within 6 months. This EtOH-HCC model is the first that can reproducibly induce liver cancer in the setting of diabetic condition and ASH. This type of tumor has extensive senescence in pericentral hepatocytes and can be targeted by senolytic compounds such as 753B. This EtOH-HCC model offers a unique tool for the study of ALD and liver cancer. Moreover, it may be used for drug screening and identification of biomarkers that discrete molecular and histological stages during multistep process of hepato-carcinogenesis in ALD Our ASH-HCC model showed additional pathological features of human alcoholic steatohepatitis including: (a) Hepatocyte ballooning indicating cell degeneration, a characteristic pathological feature in human ASH and NASH, (b) burned-out ASH, in which lipid droplets decrease as fibrosis progresses, (c) a mild rise in ALT (a liver injury marker), and (d) an increase in CK-18, a marker for NASH and ASH. A 2.385-fold increase of krt18 gene in EtOH-HCC (p=0.0187) was also observed.

In summary, our intervention using streptozotocin (STZ) and alcohol feeding induced steatosis, ASH, liver fibrosis, and HCC within 6 months. Many molecular changes in ASH-associated HCC induced by STZ/alcohol were distinct from NASH-associated HCC caused by STZ/HFD treatment. Described here is the first murine model that can reproducibly induce HCC in the setting of diabetic condition and ASH. The described ASH-HCC model provides a needed tool for the study of ALD and liver cancer. Moreover, it may be used for drug screening and identification of biomarkers for discrete molecular and histological stages during multistep process of hepato-carcinogenesis in ALD.

REFERENCES

Bacon B R, et al. (2006). *Comprehensive Clinical Hepatology*. Elsevier Health Sciences. ISBN 0-323-03675-9.

2. Schiff E R, et al. (2007). *Schiff's Diseases of the Liver, Tenth Edition.* Lippincott William & Wilkins. ISBN 0-7817-6040-2.
3. Wang B, et al. Nature, 524 (2015), pp. 180-185.
4. Ang C H, et al. "Lgr5+ pericentral hepatocytes are self-maintained in normal liver regeneration and susceptible to hepatocarcinogenesis." PNAS Sep. 24, 2019 116 (39) 19530-19540.
5. Tsai J M, et al. "Localized hepatic lobular regeneration by central-vein-associated lineage-restricted progenitors." PNAS 2017 114 (14) 3654-3659.
6. Burgada J F et al. Cell, 162 (2015), pp. 766-779.
Lin S, et al. "Distributed hepatocytes expressing telomerase repopulate the liver in homeostasis and injury." Nature (2018) 556(7700):244-248.
8. Boffetta P, et al. "The burden of cancer attributable to alcohol drinking." Int J Cancer. 2006; 119(4): 884-887.
9. Gestino G, et al. "Alcohol and hepatocellular carcinoma: a review and a point of view." World J Gastroenterol. 2014 20(43):15943-54.
10. Seitz H K, et al. "Alcoholic liver disease." In: Dancygier H, ed. *Clinical Hepatology: Principles and Practice of Hepatobiliary Diseases.* Heidelberg, Germany; Dordrecht, The Netherlands; London; New York: Springer; 2010:1111-1152.
11. Crawford J M. "Histologic findings in alcoholic liver disease." Clin Liver Dis 2012; 16: 699-716.
12. Altamirano J, et al. "Alcoholic liver disease: pathogenesis and new targets for therapy." Nat Rev Gastroenterol Hepatol. 2011 8: 491-501.
13. Welzel T M, et al. "Population-attributable fractions of risk factors for hepatocellular carcinoma in the United States." Am J Gastroenterol 2013; 108:1314-1321.
14. Davila J A, et al. "Diabetes increases the risk of hepatocellular carcinoma in the United States: a population based case control study." Gut. 2005 54(4): 533-539.
15. Fujii M, et al. "A murine model for nonalcoholic steatohepatitis showing evidence of association between diabetes and hepatocellular carcinoma." Med Mol Morphol. 2013 46(3): 141-52.
16. Klein T, et al. "Linagliptin alleviates hepatic steatosis and inflammation in a mouse model of non-alcoholic steatohepatitis." Med Mol Morphol. 2014 47(3):137-49.
17. Yoshimine Y, et al. "Hepatic expression of the Spt1c3 subunit of serine palmitoyltransferase is associated with the development of hepatocellular carcinoma in a mouse model of nonalcoholic steatohepatitis." Oncol Rep. 2015 33(4):1657-66.
18. Van Campenhout S, et al. "Myeloid-specific IRE1alpha deletion reduces tumour development in a diabetic, non-alcoholic steatohepatitis-induced hepatocellular carcinoma mouse model." Metabolism. 2020 107:154220.
19. Simoes Eugénio M, et al. "Hepatocellular Carcinoma Emergence in Diabetic Mice with Non-Alcoholic Steatohepatitis Depends on Diet and Is Delayed in Liver Exhibiting an Active Immune Response." Cancers (Basel). 2020 12(6):1491.
20. Dow M, et al. "Integrative genomic analysis of mouse and human hepatocellular carcinoma." Proc Natl Acad Sci USA. 2018 115(42):E9879-E9888.
21. van der Windt D J, et al. "Neutrophil extracellular traps promote inflammation and development of hepatocellular carcinoma in nonalcoholic steatohepatitis." Hepatology. 2018 68(4):1347-1360.
22. Lau E Y, et al "Cancer-Associated Fibroblasts Regulate Tumor-Initiating Cell Plasticity in Hepatocellular Carcinoma through c-Met/FRA1/HEY1 Signaling." Cell Rep. 2016 15(6): 1175-89.
23. Fekry B, et al. "HNF4α-Deficient Fatty Liver Provides a Permissive Environment for Sex-Independent Hepatocellular Carcinoma." Cancer Res. 2019 79(22):5860-5873.
24. Chen J, et al. "HIF-2a upregulation mediated by hypoxia promotes NAFLD-HCC progression by activating lipid synthesis via the PI3K-AKT-mTOR pathway." Aging (Albany N. Y.). 2019 11(23):10839-10860.
25. Iida A, et al. "Analysis of amino acid profiles of blood over time and biomarkers associated with non-alcoholic steatohepatitis in STAM mice." Exp Anim. 2019 68(4): 417-428.
26. Kakehashi A, et al. "Proteome Characteristics of Non-Alcoholic Steatohepatitis Liver Tissue and Associated Hepatocellular Carcinomas." Int J Mol Sci. 2017 18(2): 434.
27. Yoshida Y, et al. "Identification of unique glycoisoforms of vitamin D-binding protein and haptoglobin as biomarker candidates in hepatocarcinogenesis of STAM mice." Glycoconj J. 2018 35(5):467-476.
28. Simon Serrano S, et al. "Evaluation of NV556, a Novel Cyclophilin Inhibitor, as a Potential Antifibrotic Compound for Liver Fibrosis." Cells. 2019 8(11):1409.
29. Liebig M, et al. "n-3 PUFAs reduce tumor load and improve survival in a NASH-tumor mouse model." Ther Adv Chronic Dis. 2019 10:2040622319872118.
30. Dreval K, et al. "Gene Expression and DNA Methylation Alterations During Non-alcoholic Steatohepatitis-Associated Liver Carcinogenesis." Front Genet. 2019 29; 10:486.
31. Park J G, et al. "Connectivity mapping of angiotensin-PPAR interactions involved in the amelioration of non-alcoholic steatohepatitis by Telmisartan." Sci Rep. 2019 8; 9(1):4003.
32. Oniciu D C, et al. "Gemcabene downregulates inflammatory, lipid-altering and cell-signaling genes in the STAM™ model of NASH." PLoS One. 2018 13(5): e0194568.
33. Takakura K, et al. "Characterization of non-alcoholic steatohepatitis-derived hepatocellular carcinoma as a human stratification model in mice." Anticancer Res. 2014 34(9):4849-55.
34. Orime K, et al. "Lipid-lowering agents inhibit hepatic steatosis in a non-alcoholic steatohepatitis-derived hepatocellular carcinoma mouse model." Eur J Pharmacol. 2016 772:22-32.
35. Yokohama K, et al. "Rosuvastatin as a potential preventive drug for the development of hepatocellular carcinoma associated with non-alcoholic fatty liver disease in mice." Int J Mol Med. 2016 38(5):1499-1506.
36. Nunes Bastos R, et al. "Aurora B suppresses microtubule dynamics and limits central spindle size by locally activating KIF4A." J Cell Biol. 2013 202(4):605-21.
37. Wierstra I. "The transcription factor FOXM1 (Forkhead box M1): proliferation-specific expression, transcription factor function, target genes, mouse models, and normal biological roles." Adv Cancer Res. 2013; 118:97-398.
38. Klein M A, et al. "Biological and catalytic functions of sirtuin 6 as targets for small-molecule modulators." J Biol Chem. 2020 295(32):11021-11041.
39. Burke Z D, et al. "Liver zonation occurs through a β-catenin-dependent, c-Myc-independent mechanism." Gastroenterology. 2009 136(7): 2316-2324.e1-3.

40. Torre C, et al. "Transcription dynamics in a physiological process: β-catenin signaling directs liver metabolic zonation." Int J Biochem Cell Biol. 2011; 43:271-278
41. Vasilj A, et al. "Tissue proteomics by one-dimensional gel electrophoresis combined with label-free protein quantification." J Proteome Res. 2012; 11:3680-3689
42. Gerbal-Chaloin S, et al. "The WNT/β-Catenin Pathway Is a Transcriptional Regulator of CYP2E1, CYP1A2, and Aryl Hydrocarbon Receptor Gene Expression in Primary Human Hepatocytes." Molecular Pharmacology 2014, 86 (6) 624-634).
43. Hailfinger S, et al "Zonal gene expression in murine liver: lessons from tumors."
Hepatology 2006; 43:407-14.
44. Braeuning A, et al. "Zonal gene expression in mouse liver resembles expression patterns of Ha-ras and beta-catenin mutated hepatomas." Drug Metab Dispos 2007; 35:503-7.
45. Wise D R et al. "Glutamine addiction: a new therapeutic target in cancer." Trends Biochem Sci 2010; 35:427-33
46. Toure M, et al. "Small-Molecule PROTACS: New Approaches to Protein Degradation." Angew Chem Int Ed Engl 2016; 55:1966-73.
47. Lai A C, et al. "Induced protein degradation: an emerging drug discovery paradigm." Nat Rev Drug Discov 2017; 16:101-114
48. Veggiani G, et al. "Emerging drug development technologies targeting ubiquitination for cancer therapeutics." Pharmacol Ther 2019; 199:139-154.
49. Neklesa T K, et al. "Targeted protein degradation by PROTACs." Pharmacol Ther 2017; 174:138-144.
50. Pettersson M, et al. "PROteolysis TArgeting Chimeras (PROTACs)—Past, present and future." Drug Discov Today Technol 2019; 31:15-27.
51. Bray P F, et al. "The complex transcriptional landscape of the anucleate human platelet." BMC Genomics 2013; 14:1.
52. Kissopoulou A, et al. "Next generation sequencing analysis of human platelet PolyA+ mRNAs and rRNA-depleted total RNA." PLoS One 2013; 8:e81809.
53. He Y, et al. "Using proteolysis-targeting chimera technology to reduce navitoclax platelet toxicity and improve its senolytic activity." Nat Commun 2020; 11:1996.
54. Testino G, et al. "Alcohol and hepatocellular carcinoma: a review and a point of view." World J Gastroenterol 2014; 20:15943-54.
55. Boyault S, et al. "Transcriptome classification of HCC is related to gene alterations and to new therapeutic targets." Hepatology 2007; 45:42-52.
56. Luo Y, et al. "Oncogenic KRAS Reduces Expression of FGF21 in Acinar Cells to Promote Pancreatic Tumorigenesis in Mice on a High-Fat Diet." Gastroenterology 2019; 157:1413-1428 e11.
57. Soto-Gutierrez A, et al. "Pre-clinical and clinical investigations of metabolic zonation in liver diseases: The potential of microphysiology systems." Exp Biol Med (Maywood) 2017; 242:1605-1616.
58. Gougelet A, et al. "Hepatocellular Carcinomas With Mutational Activation of Beta-Catenin Require Choline and Can Be Detected by Positron Emission Tomography." Gastroenterology 2019; 157:807-822.
59. Knisely A S, et al. "Hepatocellular carcinoma in ten children under five years of age with bile salt export pump deficiency." Hepatology 2006; 44:478-86.
60. Yang F, et al. "Spontaneous development of liver tumors in the absence of the bile acid receptor farnesoid X receptor." Cancer Res 2007; 67:863-7.
61. Audard V, et al. "Cholestasis is a marker for hepatocellular carcinomas displaying beta-catenin mutations." J Pathol 2007; 212:345-52.
62. Childs B G, et al. "Cellular senescence in aging and age-related disease: from mechanisms to therapy." Nat Med 2015; 21:1424-35.
63. Childs B G, et al. "Senescent cells: an emerging target for diseases of ageing." Nat Rev
Drug Discov 2017; 16:718-735.
64. Kirkland J L, et al. "Cellular Senescence: A Translational Perspective." EBioMedicine 2017; 21:21-28.
65. Niedernhofer L J, et al. "Senotherapeutics for healthy ageing." Nat Rev Drug Discov 2018; 17:377.
66. Ovadya Y, et al. "Strategies targeting cellular senescence." J Clin Invest 2018; 128:1247-1254.
67. Munoz-Espin D, et al. "Cellular senescence: from physiology to pathology." Nat Rev Mol Cell Biol 2014; 15:482-96.
68. McHugh D, et al. "Senescence and aging: Causes, consequences, and therapeutic avenues." J Cell Biol 2018; 217:65-77.
69. Zhu Y, et al. "Identification of a novel senolytic agent, navitoclax, targeting the Bcl-2 family of anti-apoptotic factors." Aging Cell 2016; 15:428-35.
70. Chang J, et al. "Clearance of senescent cells by ABT263 rejuvenates aged hematopoietic stem cells in mice." Nat Med 2016; 22:78-83.
71. Yosef R, et al. "Directed elimination of senescent cells by inhibition of BCL-W and BCL-X L." Nat Commun 2016; 7:11190.

The invention claimed is:
1. A mouse model of alcohol-induced liver cancer wherein the mice have been treated with streptozotocin in an amount to induce a diabetic phenotype and fed an alcohol-containing diet.
2. The mouse model of claim 1, wherein the mice are administered streptozotocin on day 2, 3, 4, or 5 after birth.
3. The mouse model of claim 2, wherein the mice are fed the alcohol-containing diet starting on day 56±14 days after birth.
4. The mouse model of claim 3 wherein the mouse is fed the alcohol-containing diet for at least four months.
5. The mouse model of claim 1, wherein the alcohol-containing diet consists of an alcohol-liquid diet.
6. The mouse model of claim 1, wherein the alcohol-containing diet contains about 30% to about 40% of total calories from ethanol.
7. A method of screening drugs for efficacy in preventing or treating alcoholic steatohepatitis (ASH)-associated hepatocellular carcinoma (HCC) comprising administering the drugs to one or more mice of claim 1 and monitoring growth of HCC in the one or more mice.
8. A method of generating an alcohol-induced liver cancer model mouse comprising (a) administering streptozotocin to a 2-5 day old mouse in an amount sufficient to induce a diabetic phenotype in the mouse and (b) feeding the mouse an alcohol-containing diet.
9. The method of claim 8, wherein the streptozotocin is administered to the mouse on day 2 after birth.
10. The method of claim 9, wherein the alcohol-containing diet is started on day 56±14 days after birth.
11. The method of claim 10, wherein the mouse is fed the alcohol-containing diet for at least four months.
12. The mouse model of claim 8, wherein the alcohol-containing diet consists of an alcohol-liquid diet.

13. The method of claim 8, wherein the alcohol-containing diet contains about 30% to about 40% of the total calories from the ethanol.

14. A method of identifying biomarkers for hepato-carcinogenesis in alcoholic liver disease (ALD) comprising generating an alcohol-induced liver cancer model mouse as described in claim 11, analyzing gene expression in a tumor in the model mouse, and comparing expression of the same gene in an adjacent tissue in the same mouse or a control mouse, wherein an increase or decrease in expression of the gene relative to the adjacent tissue or control mouse indicates the gene is a biomarker for hepato-carcinogenesis in ALD.

\* \* \* \* \*